(12) United States Patent
Kim et al.

(10) Patent No.: US 9,493,439 B1
(45) Date of Patent: Nov. 15, 2016

(54) PROTEASOME INHIBITORS

(71) Applicant: UNIVERSITY OF KENTUCKY RESEARCH FOUNDATION, Lexington, KY (US)

(72) Inventors: Kyung-Bo Kim, Lexington, KY (US); Vinod Kasam, Malden, MA (US); Wooin Lee, Seoul (KR); Dong-Eun Kim, Seoul (KR); Zach Miller, Madison, WI (US); Chang-Guo Zhan, Lexington, KY (US); Do-Min Lee, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/680,553

(22) Filed: Apr. 7, 2015

Related U.S. Application Data

(60) Provisional application No. 61/976,220, filed on Apr. 7, 2014.

(51) Int. Cl.
C07D 401/14 (2006.01)
C07D 403/12 (2006.01)
A61K 31/4155 (2006.01)

(52) U.S. Cl.
CPC ........... C07D 401/14 (2013.01); C07D 403/12 (2013.01); A61K 31/4155 (2013.01)

(58) Field of Classification Search
CPC . C07D 401/14; C07D 403/12; A61K 31/415
See application file for complete search history.

(56) References Cited

U.S. PATENT DOCUMENTS

| 8,058,262 | B2 | 11/2011 | Bernardini et al. |
| 2005/0107307 | A1 | 5/2005 | Bernadini et al. |
| 2006/0189806 | A1 | 8/2006 | Bernardini et al. |
| 2007/0088070 | A1* | 4/2007 | Parmee ................ C07D 231/12 514/406 |
| 2011/0070297 | A1* | 3/2011 | Cao ...................... C07D 231/12 424/450 |
| 2012/0190665 | A1 | 7/2012 | Gibbons et al. |

FOREIGN PATENT DOCUMENTS

| JP | WO 0132173 A1 * | 5/2001 | ............. A61K 31/41 |
| JP | WO 2006109680 A1 * | 10/2006 | .......... C07D 231/12 |
| JP | 2011042591 A * | 3/2011 | |
| WO | 2007104558 | 9/2007 | |

OTHER PUBLICATIONS

Humne et al. "Selective O-deallylation of dihydropyrazoles by molecular iodine in the presence of active N-allyl and formyl groups" Res. Chem. Intermed. 2013, 39, 585-595.*
Vasilevich et al. "Dual mode of action of phenyl-pyrazole-phenyl (6-5-6 system)-based PPI inhibitors: alpha-helix backbone versus alpha-helix binding epitope" Med. Chem. Commun. 2013, 4, 1597-1603.*
Miller, Z., Kim, K.S., Lee, D.M., Kasam, V., Baek, S.E., Lee K.H., Zhang, Y.Y., Ao, L., Carmony, K.C., Lee, N.R., Zhou, S., Zhao, Q., Jang, Y., Jeong, H.Y., Zhan, C.G., Lee, W., Kim, D.E., Kim, K.B., Proteasome inhibitors with pyrazole scaffolds from structure-based virtual screening, J Med Chem, 58, 2036-2041.

* cited by examiner

*Primary Examiner* — Joseph Kosack
*Assistant Examiner* — Amanda L Aguirre
(74) *Attorney, Agent, or Firm* — Stites & Harbison PLLC; Mandy Wilson Decker

(57) ABSTRACT

Compounds of formula (I)

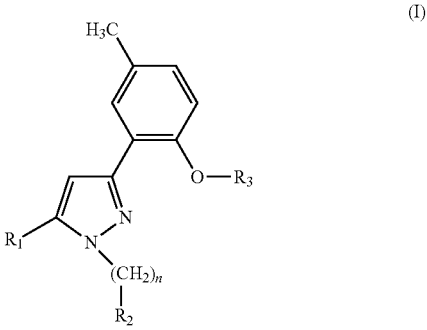

are useful for inhibiting a proteasome in a cell. Compounds, pharmaceutical compositions and methods of use are provided herein.

20 Claims, 10 Drawing Sheets

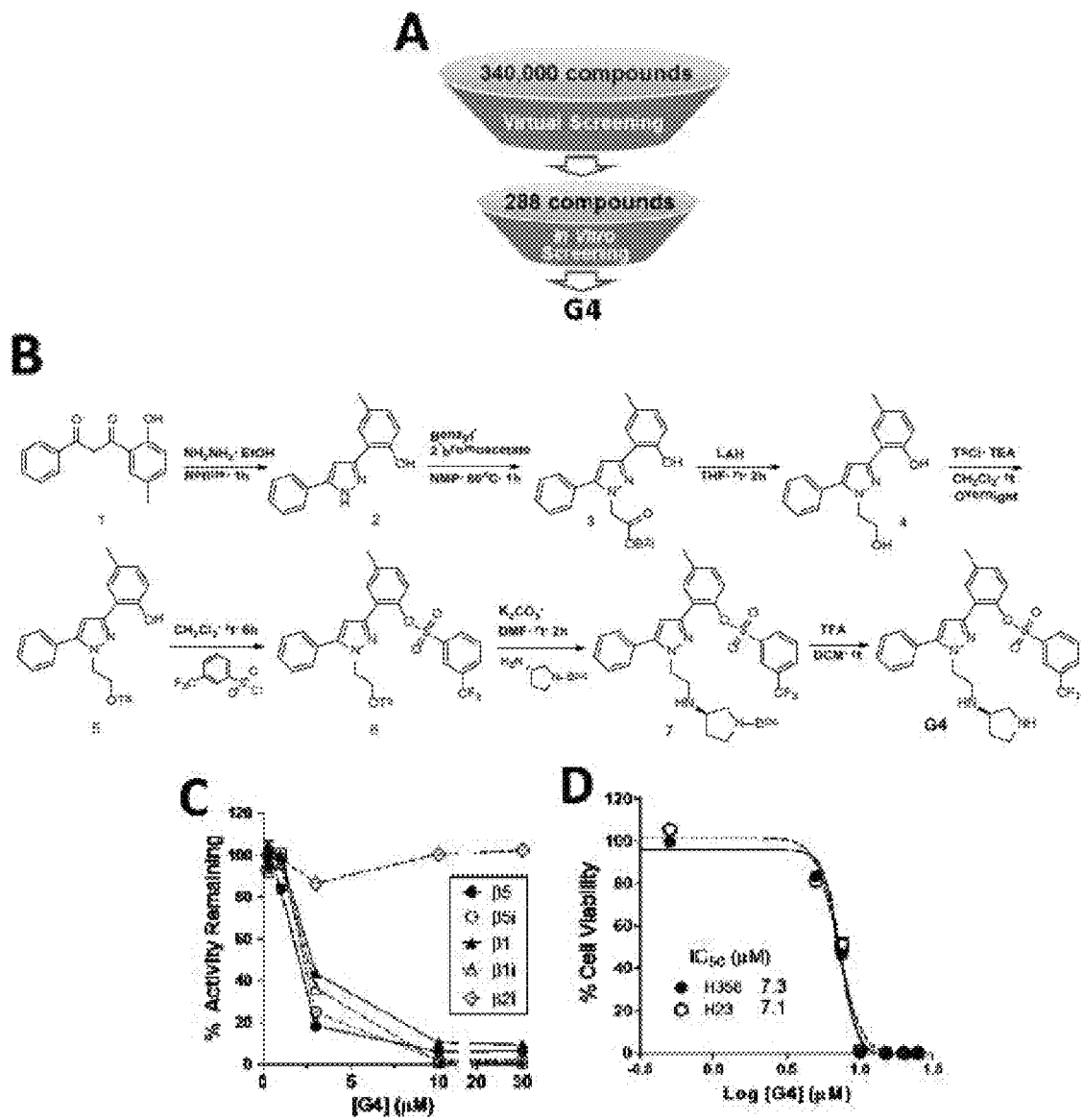
FIGS. 2A-D

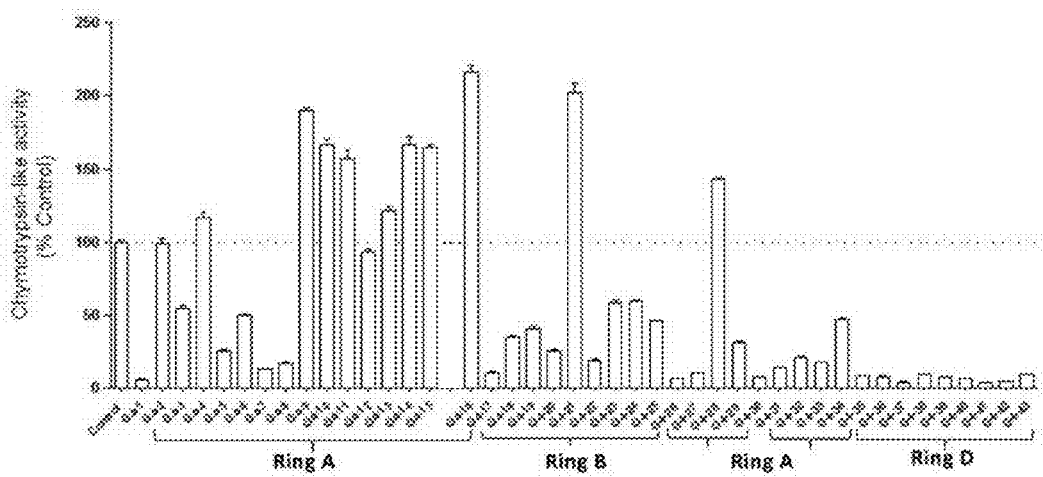
FIG. 3E
| Compound: | G4 | G4-1 | G4-40 | G4-41 | G4-42 |
|---|---|---|---|---|---|
| CT-L Activity Remaining at 10 µM: | 3.69 ± 0.35% | 6.15 ± 0.17% | 6.59 ± 0.01% | 3.95 ± 0.06% | 4.58 ± 0.08% |
| Panc-1 72-hour Cell Viability at 25 µM: | 0.01 ± 0.003% | 0.05 ± 0.01% | 1.43 ± 0.08% | 96.35 ± 1.03% | 97.65 ± 0.63% |
FIG. 3F
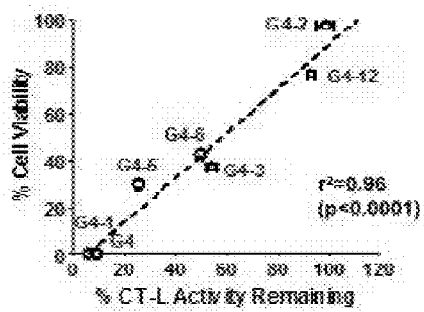
FIG. 3G

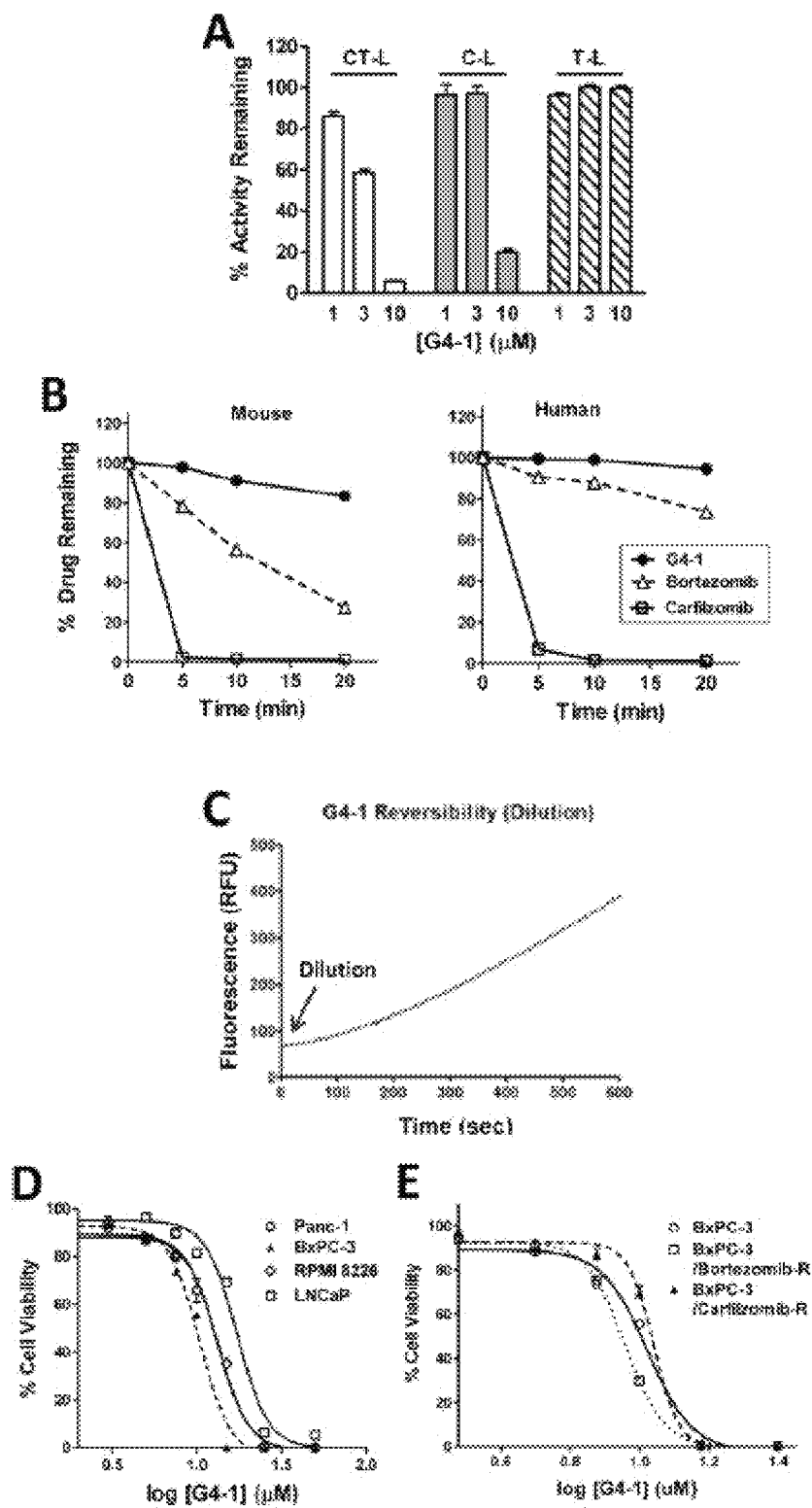
FIGS. 5A-E

| Cell Line | G4-1 | | Carfilzomib | | Bortezomib | |
|---|---|---|---|---|---|---|
| | $IC_{50}$ (µM) | Fold change | $IC_{50}$ (nM) | Fold change | $IC_{50}$ (nM) | Fold change |
| BxPC-3 | 10.5 | - | 21.5 | - | 10.6 | - |
| BxPC-3/ Carfilzomib-R | 11.0 | 1.0x | 109.4 | 10.4x | 41.9 | 4.0x |
| BxPC-3/ Bortezomib-R | 9.1 | 0.9x | 141.6 | 13.5x | 105.4 | 10.0x |

FIGS. 5F

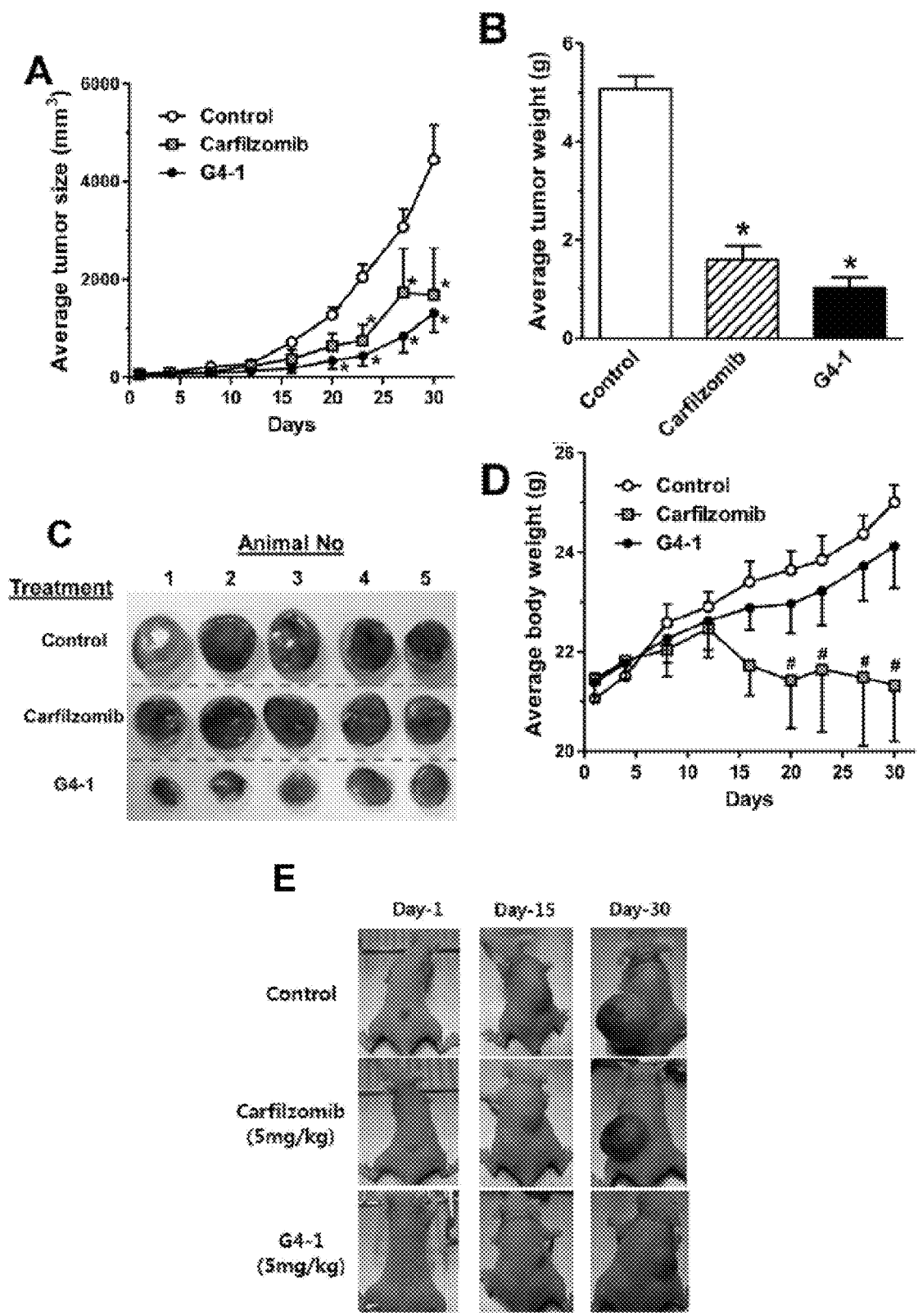
FIGS. 6A-E

PROTEASOME INHIBITORS

RELATED APPLICATIONS

This application claims priority from U.S. Provisional Application Ser. No. 61/976,220 filed Apr. 7, 2014, the entire disclosure of which is incorporated herein by this reference.

GOVERNMENT INTEREST

This invention was made with government support under R01 CA128903 awarded by National Institutes of Health. The government has certain rights in the invention.

TECHNICAL FIELD

The presently-disclosed subject matter relates to novel non-peptide proteasome inhibitors, their pharmaceutically acceptable salts, process(es) for their preparation, pharmaceutical compositions containing the novel non-peptide proteasome inhibitors, and methods of treating disease(s) in a subject, including cancer, via administration of the non-peptide proteasome inhibitors.

INTRODUCTION

The proteasome is a key player in one of the most fundamental processes in eukaryotic cells, the ubiquitin-dependent protein degradation pathway. The proteasome is a large multi-subunit protease that degrades the majority of cellular proteins. The proteasome also controls critical cellular process, such as the cell cycle, via the regulated degradation of signaling proteins. By perturbing these processes, inhibition of the proteasome leads to apoptosis, especially in cancer cells. It is for this reason that proteasome inhibitors have become critically important therapies in the treatment of multiple myeloma.

The barrel-shaped 20S core of the proteasome consists of four stacked heptameric rings: two outer α-rings and two inner β-rings (FIG. 1A). While the two outer α-rings serve mainly structural roles, the two inner β-rings have three catalytic subunits in each ring. In mammalian cells, there exist two main proteasome subtypes: the constitutive proteasome (CP) and the immunoproteasome (IP). These two proteasome subtypes differ by the incorporation of two distinct sets of catalytic subunits. The CP contains the catalytic subunits $\beta 1$, $\beta 2$, and $\beta 5$, which cleave peptide bonds after acidic (Caspase-Like, C-L), basic (Trypsin-Like, T-L) and hydrophobic (Chymotrypsin-Like, CT-L) residues, respectively. (2) The CP is expressed in all eukaryotic cells and plays key roles in many important intracellular processes, such as cell cycle progression, development, and inflammation. On the other hand, the immunoproteasome is expressed in immune cells and can be induced in other cell types upon exposure to inflammatory cytokines, such as interferon-γ (INF-γ) and tumor necrosis factor-alpha (TNF-α). (3)

The 20S immunoproteasome core is structurally identical to the constitutive proteasome except for the incorporation of catalytic subunits $\beta 1i$, $\beta 2i$, and $\beta 5i$ instead of $\beta 1$, $\beta 2$, and $\beta 5$, respectively (FIG. 1B). The catalytic activities of the immunoproteasome subunits $\beta 2i$ and $\beta 5i$ are relatively similar to that of their constitutive proteasome counterparts, possessing T-L and CT-L activity, respectively. In contrast, the replacement of $\beta 1$ with $\beta 1i$ results in a more significant change in the cleavage specificity from C-L to CT-L.

Although the distinct catalytic subunits of the different proteasome isoforms have been suggested to play roles in adding antigenic diversity to peptides generated from protein degradation, the catalytic subunits responsible for the CT-L activity ($\beta 5$ and $1350$ are thought to be most physiologically important and have been recognized as the key targets of bortezomib and carfilzomib.

Due to the crucial roles of proteasomes in rapidly proliferating cells such as cancer cells, the proteasome has been exploited as a cancer target, resulting in bortezomib (Velcade®), the first-in-class proteasome inhibitor approved by the FDA in 2003 for the treatment of relapsed multiple myeloma (MM). In 2012, a second-generation proteasome inhibitor carfilzomib was approved by the FDA for the treatment of relapsed multiple myeloma patients who have received at least two prior therapies, including bortezomib. The addition of these proteasome inhibitors to chemotherapeutic armaments has dramatically improved the therapeutic landscape for patients with multiple myeloma (MM). Despite the remarkable successes of these drugs in the clinic, intrinsic and acquired drug resistance remains a major clinical challenge. Additionally, these drugs have failed to provide clinical benefit to patients with solid cancers, further adding to the need for next generation proteasome inhibitors.

Proteasome inhibitors are drugs designed to block and/or inhibit the ability of cancer cells to use certain proteins to carry out the cell cycle. When they are unable to complete this process, the result is the death of the cell. Currently, just a few proteasome inhibitors are available on the market, but they are in wide use. They are: Velcade® and Kyprolis®.

VELCADE® (bortezomib) is a targeted treatment, meaning it does not kill cells indiscriminately but rather has a molecular target it seeks out. VELCADE® is FDA approved to treat multiple myeloma (a type of bone marrow cancer) as well as patients with mantle cell lymphoma who have failed first-line therapy.

KYPROLIS® (carfilzomib) is the second generation proteasome inhibitor approved by the FDA in 2012 for the treatment of patients with relapsed/refractory multiple myeloma who have received at least two prior therapies including bortezomib. Phase II clinical trials found that its response rate is just under 25% with median duration of response of 7.8 months and overall survival of ~16 months. Compared to VELCADE®, KYPROLIS® is shown to be a more selective proteasome inhibitor with reduced off target side effects such as peripheral neuropathy.

In the last decade, the FDA approvals of the proteasome inhibitors bortezomib and carfilzomib have greatly improved the therapeutic landscape for patients with multiple myeloma. Indeed, these FDA approvals have validated the proteasome as an important target in the treatment of multiple myeloma. Despite these exciting advancements, there is still much work to be done to provide inhibitors which overcome intrinsic and acquired drug resistance, which have clinical utility outside of multiple myeloma, and which have improved pharmacokinetic properties.

Accordingly, the subject matter of the present disclosure relates to the development of novel proteasome inhibitors and that have improved pharmacokinetic properties and broader and/or unique treatment applications as compared to compounds known in the art.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The present disclosure includes non-peptide proteasome inhibitor, including a compound of formula (I), a pharmaceutically acceptable salt, solvate, or physiologically functional derivative thereof:

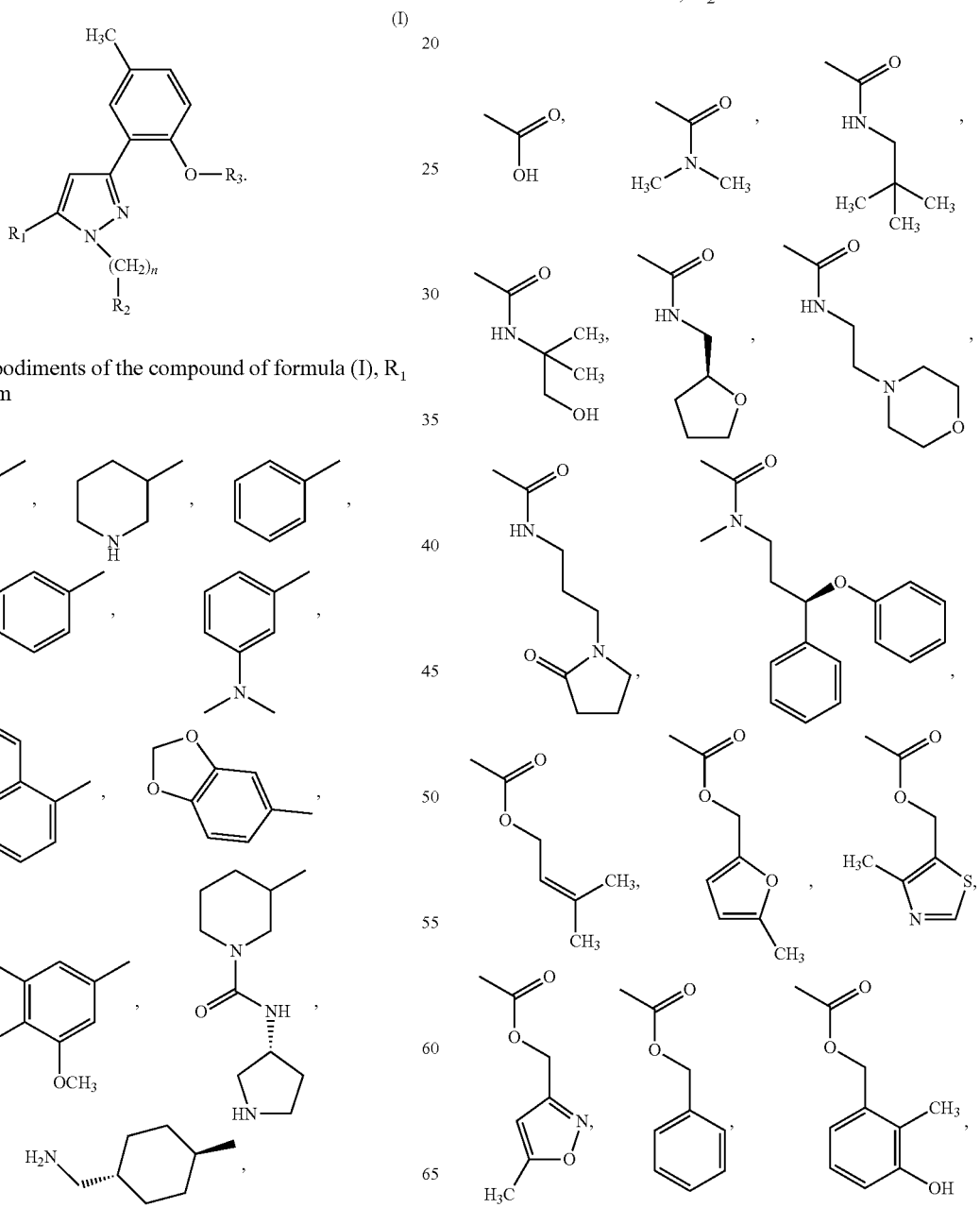

In some embodiments of the compound of formula (I), $R_1$ is selected from

In some embodiments, $R_2$ is selected from

-continued
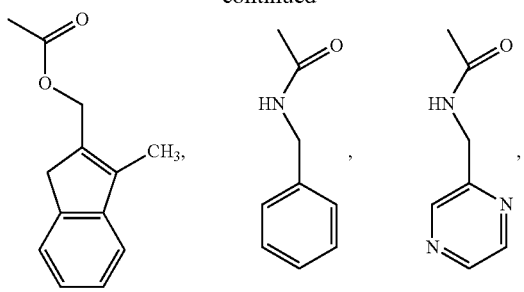
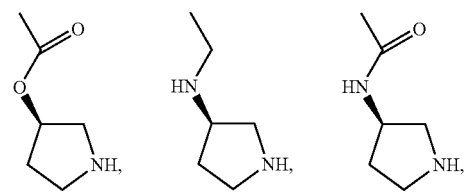
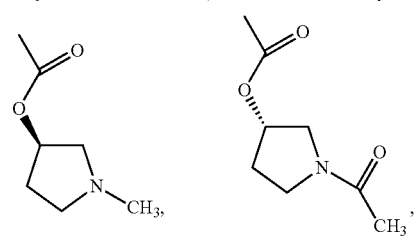
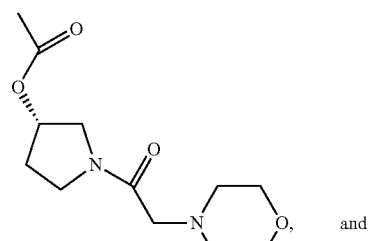
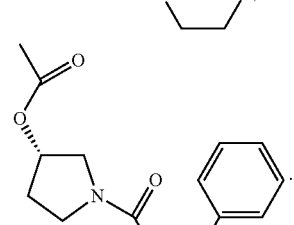
In some embodiments, $R_3$ is selected from
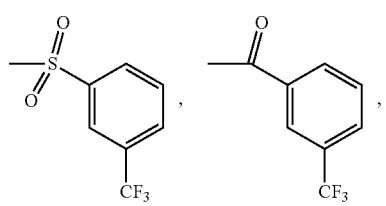
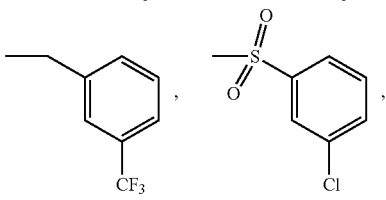
-continued
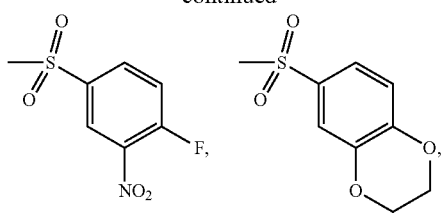
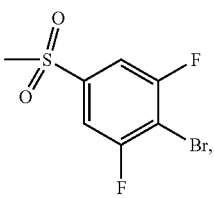
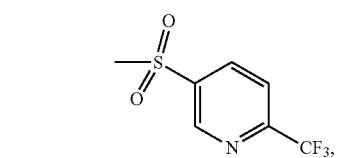
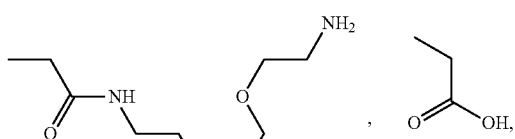
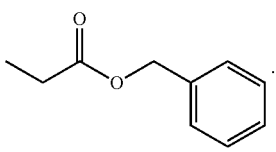
In some embodiments, n is 0, 1, or 2.
In certain embodiments of the compound of formula (I), $R_1$ is selected from
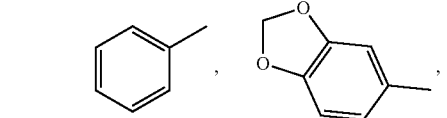
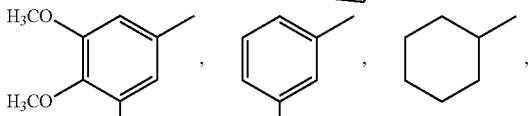
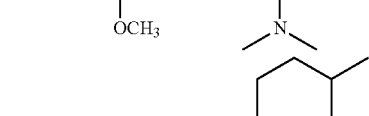
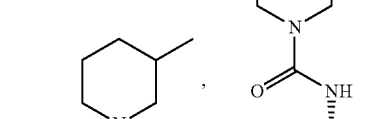

-continued
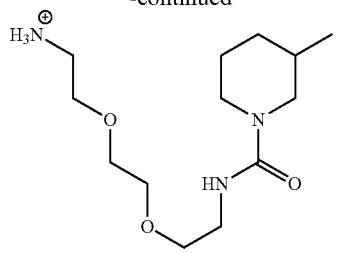
In some embodiments, R₂ is selected from
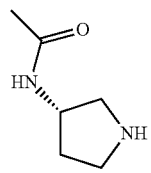 and 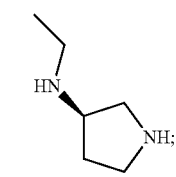;
and n is 0 or 1.
In some embodiments, R₃ is selected from
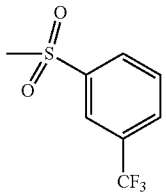 and 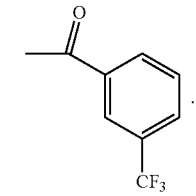.
In some embodiments of the compound of formula (I), R₂ is
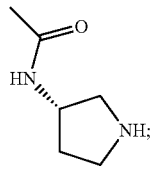
and n is 0 or 1.
In some embodiments R₃ is
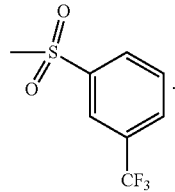
In some embodiments of the compound of formula (I), R₃ is
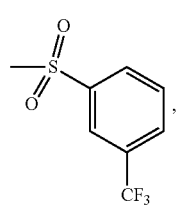,
R₂ is
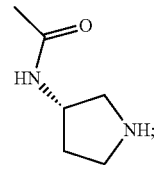
and n is 0 or 1.
In some embodiments, the compound of formula (I) is in accordance with the following formula(ae):
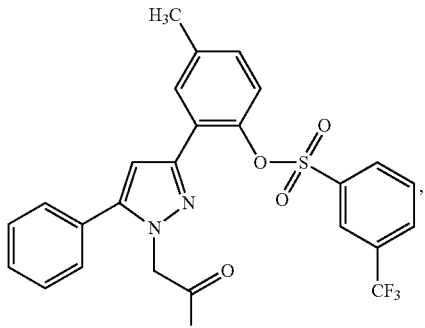
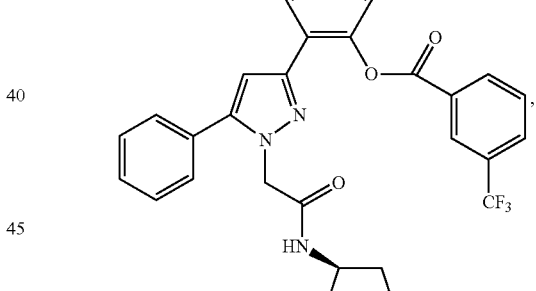
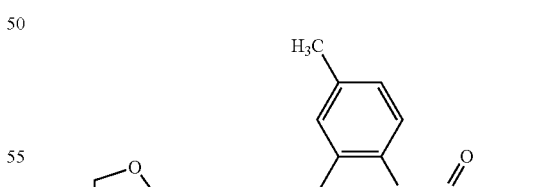
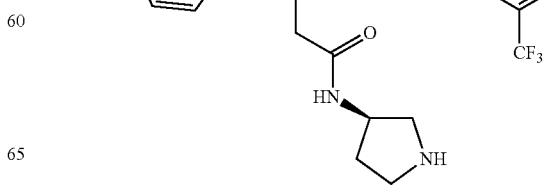

-continued

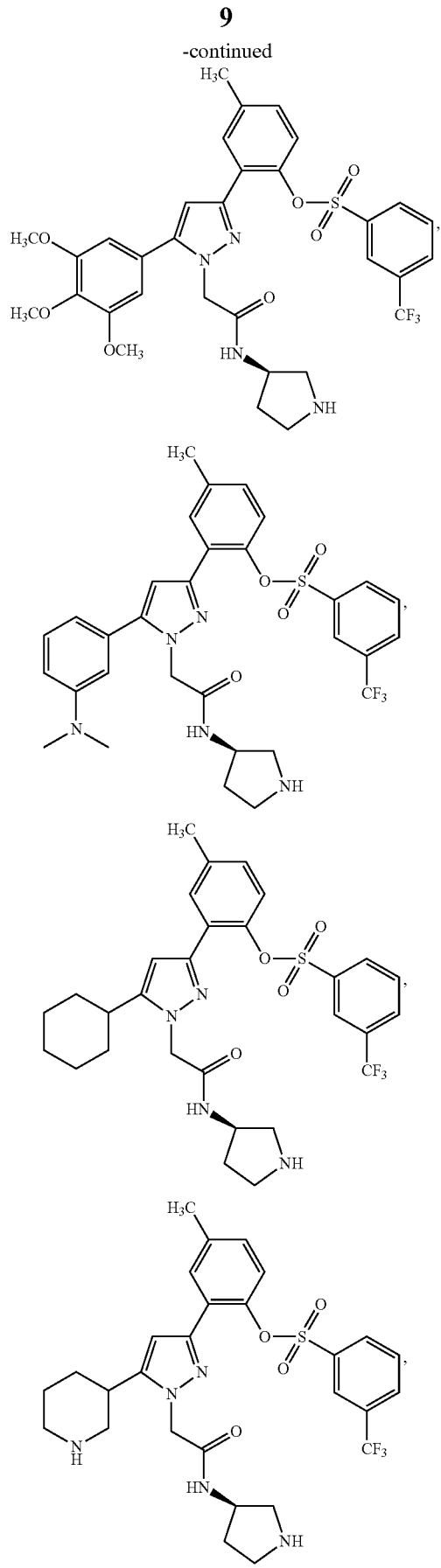

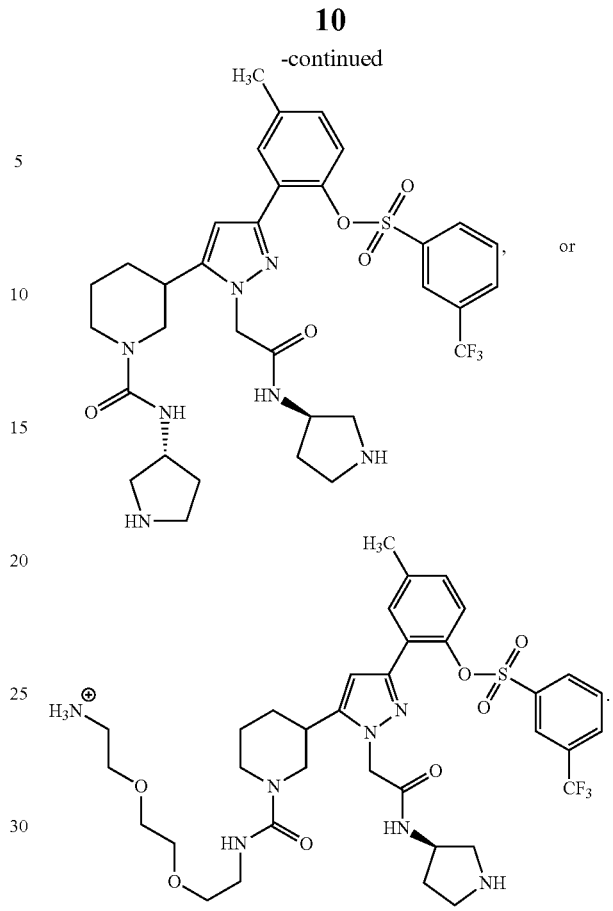

The presently-disclosed subject matter further includes a pharmaceutical composition, which includes at least one compound according to formula (I) and a pharmaceutically-acceptable carrier.

The presently-disclosed subject matter also includes a method of inhibiting a proteasome in a cell, which involves administering or contacting the compound of formula (I) to the cell. The administrating or contacting the compound to the cell can lead to apoptosis of the cell. The cell can be, for example, a cancer cell.

The presently-disclosed subject matter also includes a method of treating a disease in a subject, which includes administering an effective amount of a pharmaceutical composition containing the compound of formula (I) to the subject. The disease can be, for example, a cancer.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 2A shows the step-wise screening process employed to identify non-peptide proteasome inhibitors of the present disclosure. FIG. 2B provides a synthetic scheme of G4. FIG. 2C illustrates properties of G4, one of the compounds that selectively inhibits subunits responsible for the CT-L and C-L activities ($\beta 5$, $\beta 5i$, $\beta 1$ and $\beta 1i$), but not for the T-L activity ($\beta 2i$) Purified 20S immunoproteasome and constitutive proteasome were used. FIG. 2D shows that G4 induces cancer cell death in lung cancer cell lines with $IC_{50}$ values of ~7 μM.

FIG. 3E provides screening results of G4 analogs against the CT-L activity of purified constitutive proteasome. FIG. 3F illustrates the cytotoxicity of selected compounds in Panc-1 cells. FIG. 3G illustrates the correlation between the inhibitory potency against the CT-L activity and cytotoxic effects of G4 analogs.

FIG. 5A shows that G4-1 is effective in inhibiting CT-L and C-L activities of proteasomes in RPMI 8226 cell extracts. The inhibitory effects of G4-1 on the CT-L, C-L and T-L activities were measured by assessing the hydrolysis of the fluorogenic proteasome substrates Suc-LLVY-AMC, Z-LLE-AMC and Boc-LRR-AMC, respectively. FIG. 5B demonstrates that as compared to carfilzomib (Cfz) and bortezomib (Btz), compound G4-1 has excellent metabolic stability when tested using liver microsomes prepared from Balb/c mice and BD UltraPooJT" human liver microsomes. FIG. 5C provides a reaction progress curve with 30 min preincubation of RPMI 8226 cell extracts and G4-1. The upward curvature demonstrates that the proteasome was recovering and that the reaction was reversible. FIG. 5D shows that G4-1 effectively induced cell death in multiple cancer cell lines. FIG. 5E includes the potency of G4-1 in inducing cell death in BxPC-3 cell lines with acquired resistance to bortezomib or carfilzomib. FIG. 5F provides a comparison of $IC_{50}$ values of BxPC-3 sublines resistant to carfilzomib or bortezomib to its parental cell lines.

FIG. 6 demonstrates that G4-1 inhibits tumor growth in vivo. Male nude mice bearing LNCaP tumors received intraperitoneal injections of either G4-1 (5 mg/kg), carfilzomib (5 mg/kg), or vehicle alone (8% DMSO in HP-$\beta$-cyclodextrin and sodium citrate) twice a week for 4 weeks (n=5 mice/group). Results are expressed as mean and standard deviation. FIG. 6A presents tumor growth curves in animals receiving the respective treatments (*, p<0.001, significantly different from the control group, two-way ANOVA followed by Bonferroni post tests). FIG. 6B & FIG. 6C provide average weights and images of tumors isolated at the end of the experimental period (*, p<0.001, significantly different from the control group, one-way ANOVA followed by Newman-Keuls post tests). FIG. 6D shows average body weights of mice receiving the respective treatments (#, p<0.01, significantly different from both G4-1 and control groups, two-way ANOVA followed by Bonferroni post tests). FIG. 6E includes representative images of mice at the end of the experimental period.

DESCRIPTION OF EXEMPLARY EMBODIMENTS

Figures 1A, 1B, 1C:
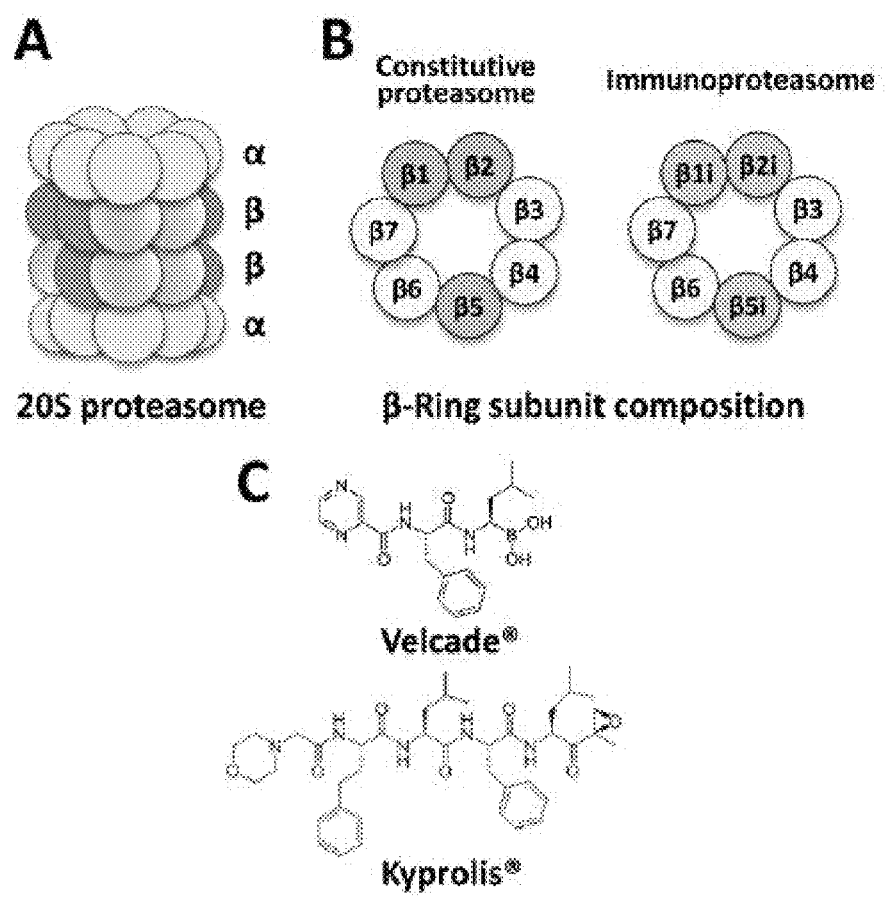
FIG. 1A illustrates the 26S proteasome, which is composed of a 20S core and 19S regulatory complex.
FIG. 1B presents a schematic representation of subunit composition within a 20S proteasome core. Each β-ring contains three catalytic subunits.
FIG. 1C provides the chemical structure of two FDA-approved proteasome inhibitors, bortezomib (Velcade®) and carfilzomib (Kyprolis®).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Although any methods, devices, and materials similar or equivalent to those described herein can be used in the practice or testing of the presently-disclosed subject matter, representative methods, devices, and materials are now described.

Unless otherwise indicated, the term "administering" is inclusive of all means known to those of ordinary skill in the art for providing a preparation to a subject, including administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and/or subcutaneous administration. Administration can be continuous or intermittent. A preparation can be administered therapeutically; that is, administered to treat an existing condition of interest. A preparation can be administered prophylactically; that is, administered for prevention of a condition of interest.

In some embodiments a subject will be administered an effective amount of at least one compound provided in the present disclosure. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

The term "physiologically functional derivative" means any pharmaceutically acceptable derivative of a compound of the present disclosure. For example, an amide or ester of a compound of formula (I), which upon administration to a subject, particularly a mammal, is capable of providing, either directly or indirectly, a compound of the present disclosure of an active metabolite thereof.

As will be recognized by one of ordinary skill in the art, the terms "suppression," "suppressing," "suppressor," "inhibition," "inhibiting" or "inhibitor" do not refer to a complete elimination of angiogenesis in all cases. Rather, the skilled artisan will understand that the term "suppressing" or "inhibiting" refers to a reduction or decrease in angiogenesis. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments the subject in need thereof will be suffering or will have been diagnosed with one or more neoplastic or hyperproliferative diseases, disorders, pathologies, or conditions. Examples of such diseases, conditions, and the like include, but are not limited to, neoplasms (cancers or tumors) located in the colon, abdomen, bone, breast, digestive system, esophagus, liver, pancreas, peritoneum, endocrine glands (adrenal, parathyroid, pituitary, testicles, ovaries, cervix, thymus, thyroid), eye, head and neck, nervous (central and peripheral), lymphatic system, pelvis, skin, soft tissue, spleen, thoracic areas, bladder, and urogenital system. Other cancers include follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer, or metastases thereof.

A subject may also be in need thereof because they have acquired diseases or conditions associated with abnormal and increased cell survival such as, but are not limited to, progression and/or metastases of malignancies and related disorders such as leukemia (including acute leukemias (e.g., acute lymphocytic leukemia, acute myelocytic leukemia, including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and/or retinoblastoma. The conditions, diseases, and the like described above, as well as those that will be apparent to those of ordinary skill in the art, are collectively referred to as "cancer" herein.

As used herein, the terms "treatment" or "treating" relate to any treatment of a condition of interest, including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

Moreover, the subject matter of the present disclosure relates to the development of novel proteasome inhibitors that utilize a non-peptide scaffold. Indeed, the proteasome inhibitors of the present disclosure avoid the use of peptide backbone(s) and/or reactive pharmacophores. In some embodiments, the non-peptide inhibitors of the present disclosure comprise a substituted pyrazole scaffold, which provides for relatively potent inhibition of proteasome activity without relying on a peptide-based structure of a reactive pharmacophore. In some embodiments, the subject matter of the present disclosure is directed to reversible, non-peptide, non-covalent inhibitors of the 20S proteasome. The proteasome inhibitors of the present disclosure have improved pharmacokinetic properties and broader treatment applications than those previously known in the art. In some embodiments, the non-peptide proteasome inhibitors of the present disclosure demonstrate activity against multiple solid cancer cell lines, including cell lines with acquired resistance to bortezomib and/or carfilzomib.

The FDA approval of the peptide-based proteasome inhibitors bortezomib and carfilzomib in 2003 and 2012, respectively, has validated the proteasome as an important target in the treatment of multiple myeloma. Additionally, these inhibitors have demonstrated in vitro as well moderate in vivo efficacy in preclinical models of solid tumors. Despite this, clinical trials utilizing these drugs for the treatment of solid tumors have shown disappointing results. Although the reasons for these failures remain unclear, one possibility is that existing proteasome inhibitors such as bortezomib and carfilzomib lack the pharmacokinetic and pharmacodynamics properties needed to sufficiently inhibit proteasomes in solid tumors.

Proteasome inhibitors approved by the FDA are currently used for the treatment of multiple myeloma and mantle cell lymphoma. Despite strong indications of activity in preclinical models, proteasome inhibitors in the clinic have failed to provide clinical benefits for solid cancer patients, presumably due to poor metabolic stability. Research indicates that this is due to structural and functional properties of these inhibitors which are shared P1's in clinical development-the reliance on a peptide backbone coupled with an electrophilic warhead to mediate covalent binding to the proteasome. It is believed that it is the structural and functional properties of known proteasome inhibitors which explain the high failure rate of those proteasome inhibitors in patients with solid tumors. (20, 36)

With this in mind, it has been postulated that reversible, non-peptide proteasome inhibitors could be developed with improved properties and that these inhibitors could serve both as novel tools to advance the understanding of the proteasome and as potential therapeutic options for the treatment of solid tumors.

In order to identify novel proteasome inhibitors with non-peptide scaffolds, the present inventor(s) conducted an in silico screen of more than 340,000 structures followed by in vitro assays using purified proteasomes. This screening effort lead to several novel non-peptide compounds of interest.

One such compound, a substituted pyrazole derivative, was used to synthesize a small library of analogues. The analogue compounds were evaluated for their ability to inhibit proteasome catalytic activity using specific fluorogenic substrates, and a structure-activity relationship was developed. In vitro cell viability assays were conducted against non-small cell lung cancer (NSCLC), pancreatic, prostate and multiple myeloma cell lines. The in vivo antitumor activity of the most promising analogue was also determined using a prostate cancer xenograph model.

Moreover, the substituted pyrazole derivative was found to have reversible inhibitory activity against the chymotrypsin-like subunits of the 20S constitutive proteasome and immunoproteasome with single-micromolar $IC_{50}$ values. It was equipotent against a series of cancer cell lines including bortezomib-resistant and carfilozmib-resistant cancer cell lines, despite varied sensitivity to bortezomib and carfilzomib. $IC_{50}$ values against these cell lines were less than 10 μM. Using the analogue with improved potency and promising drug-like properties, inhibition of in vivo tumor growth was also observed.

In some embodiments, the present disclosure provides a non-peptide proteasome inhibitor of formula (I), a pharmaceutically acceptable salt, solvate, or physiologically functional derivative thereof:

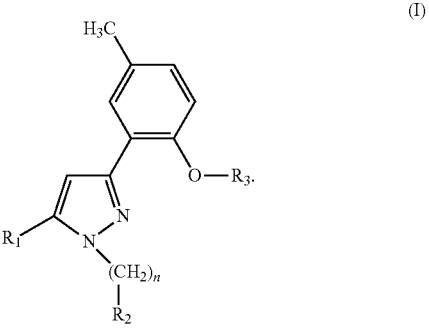

In certain embodiments of the non-peptide proteasome inhibitor of formula I, $R_1$ is chosen from:

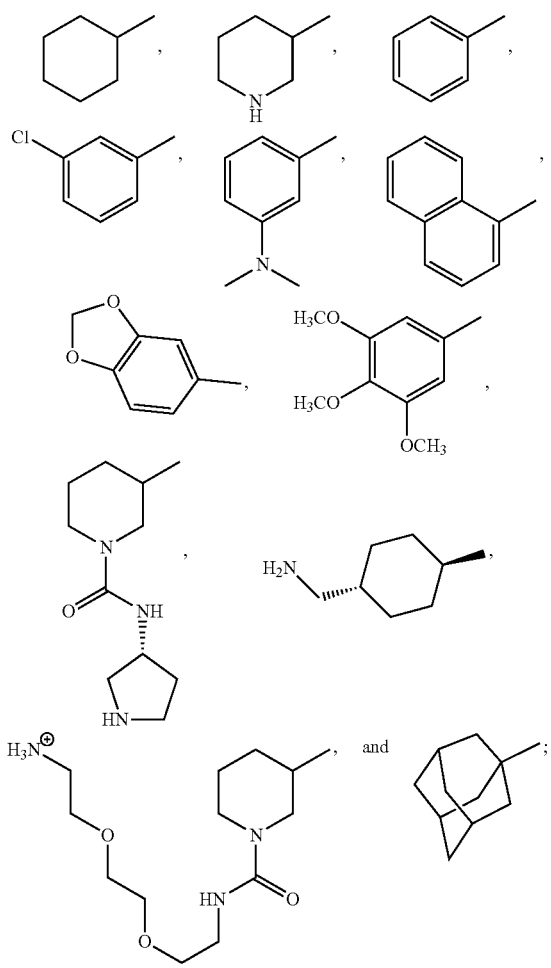

$R_2$ is selected from

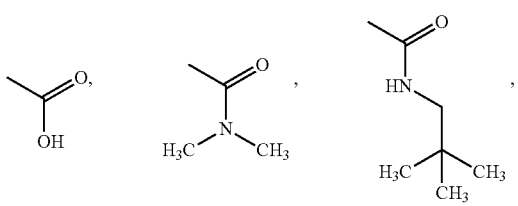

17
-continued
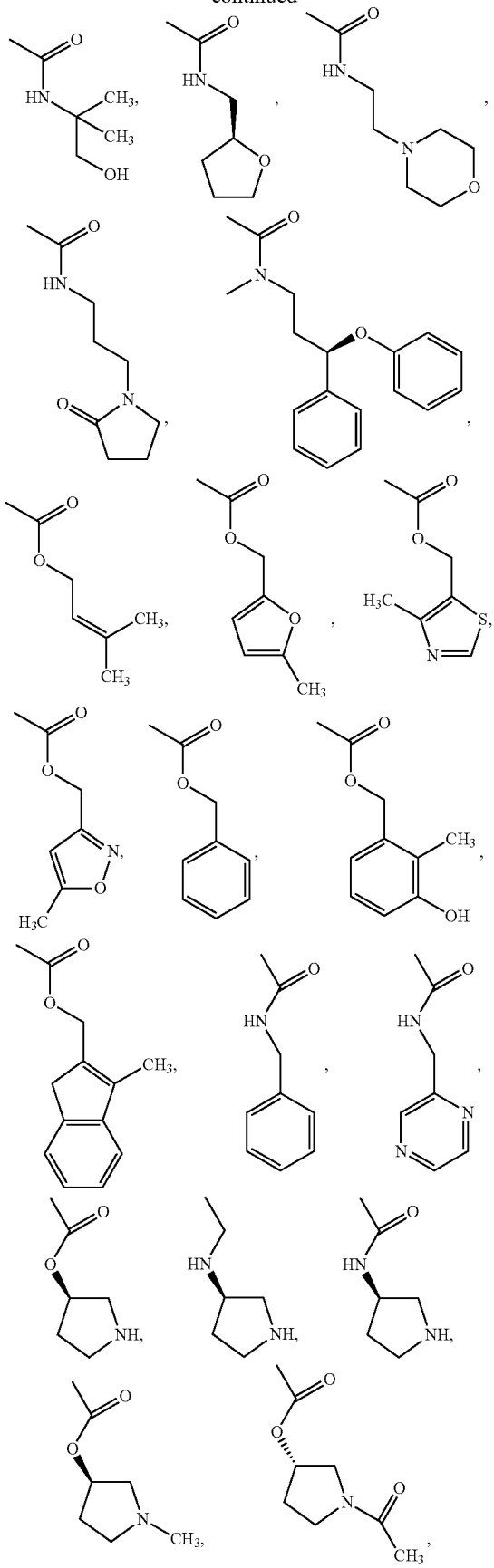
18
-continued
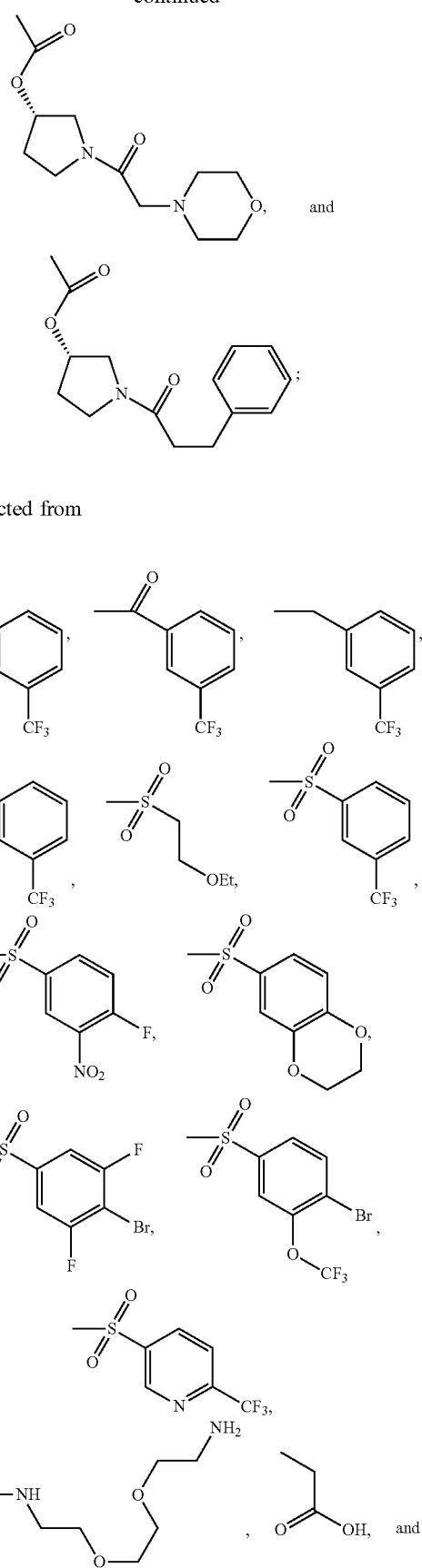
$R_3$ is selected from

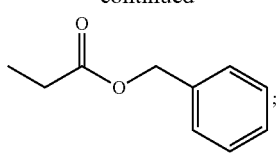
and n is selected from 0, 1, or 2.
In certain embodiments of the non-peptide proteasome inhibitor of formula I, $R_1$ is
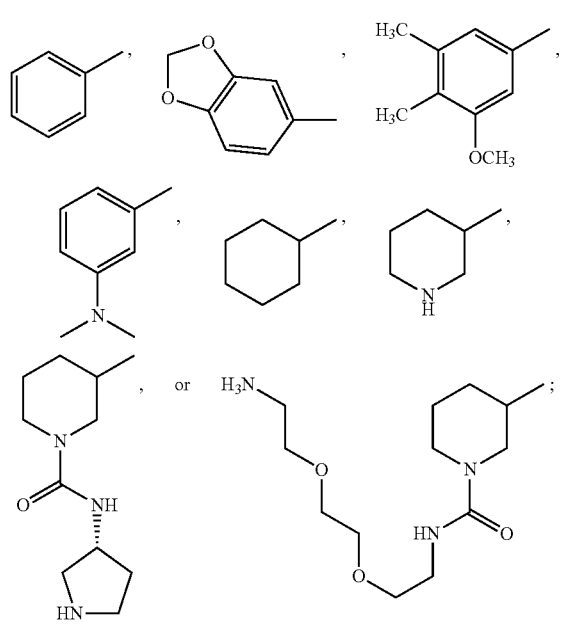
$R_2$ is selected from
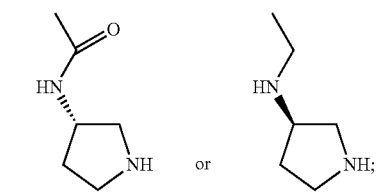
and $R_3$ is selected from
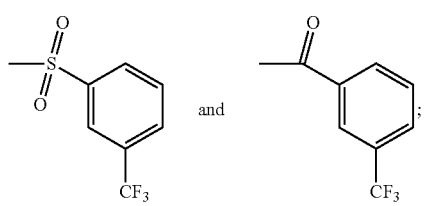
and n is 0 or 1.
In certain embodiments of the non-peptide proteasome inhibitor of formula I, $R_1$ is
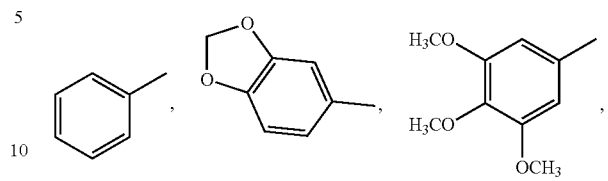
$R_2$ is
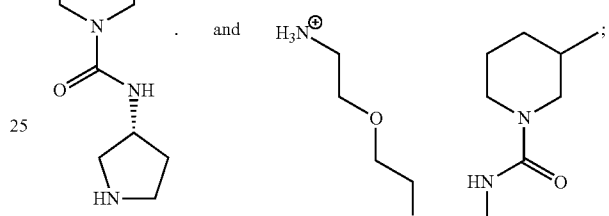
and $R_3$ is
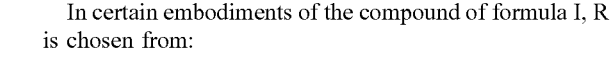
and; and n is 0 or 1.
In certain embodiments of the compound of formula I, $R_1$ is chosen from:
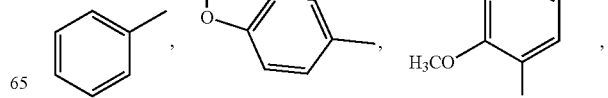

-continued

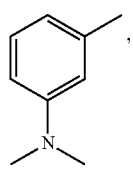 , 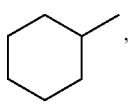 , 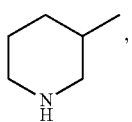 ,

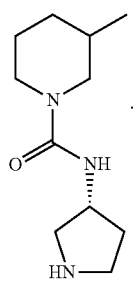 and 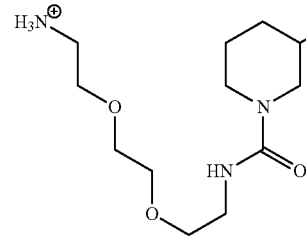.

In certain embodiments of the compound of formula I, $R_2$ is chosen from:

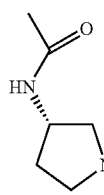 and 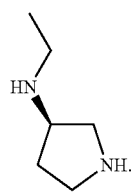.

In some embodiments, n is 0 or 1.

In certain embodiments of the compound of formula I, $R_3$ is chosen from:

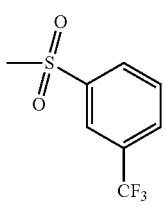 and 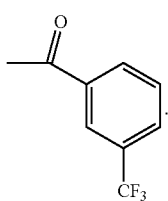.

In certain embodiments, $R_2$ is

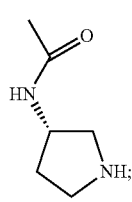

and n is 0 or 1.

In certain embodiments, $R_3$ is

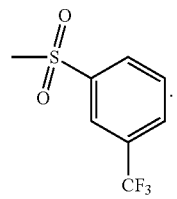

In certain embodiments, $R_2$ is

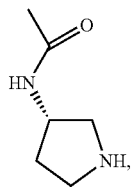, n is 0 or 1, and $R_3$ is

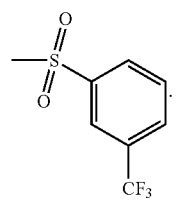

In some embodiments, the compound is according to the formula:

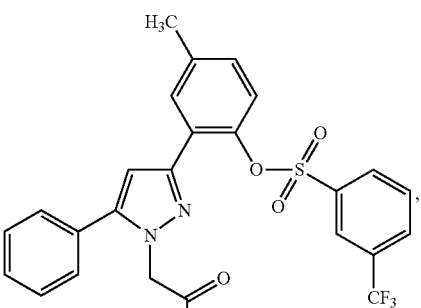

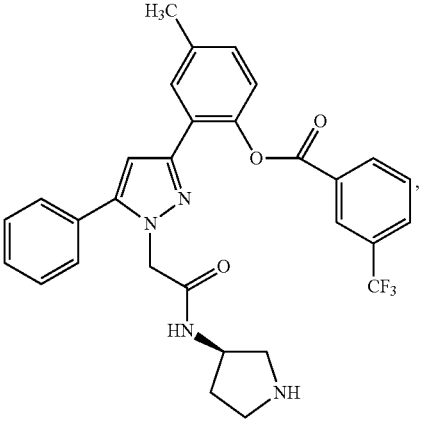

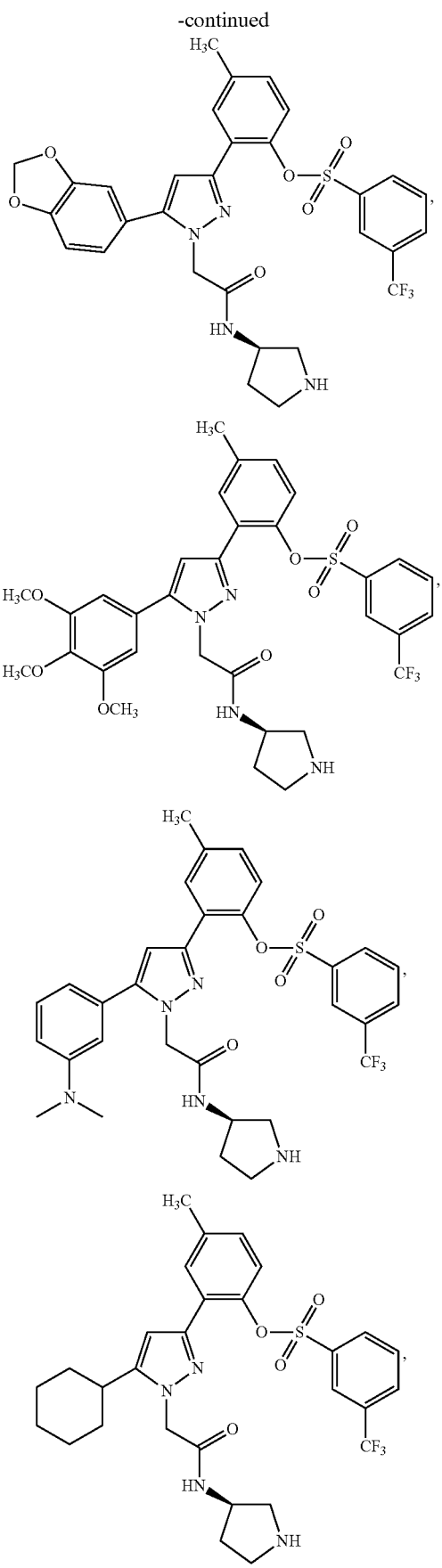
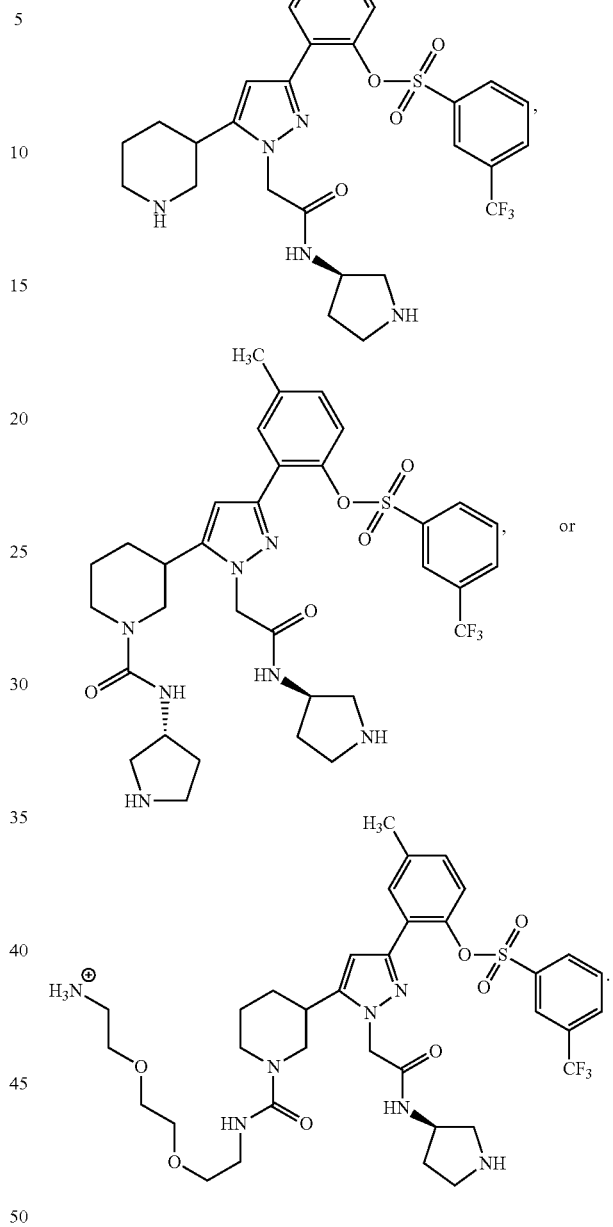

Certain compounds of formula (I) may exist in stereoisomeric forms (e.g., they may contain one or more asymmetric carbon atoms, or they may exhibit cis-trans isomerism), and, the individual stereoisomers and mixtures of these are included within the scope of the present disclosure.

The novel non-peptide proteasome inhibitors of the present disclosure may be used for the treatment of a disease or condition, such as cancer. In some embodiments, there is provided a pharmaceutical composition for use in the treatment (including prophylaxis) of one or more conditions or indications set forth herein, which comprises a compound of formula I, a pharmaceutically acceptable salt, solvate, or physiologically functional derivative thereof, and a pharmaceutically acceptable carrier or excipient.

Processes for preparing a pharmaceutically acceptable salt, solvate and/or a physiologically functional derivative of the compound(s) of formula (I) are conventional in the art.

The presently-disclosed subject matter further includes pharmaceutical compositions of the compounds as disclosed herein, and further includes a pharmaceutically-acceptable carrier. In this regard, the term "pharmaceutically acceptable carrier" refers to sterile aqueous or non-aqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

The presently-disclosed subject matter further includes a kit that can include a compound or pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

Still further, the presently-disclosed subject matter includes a method for treating cancer. In some embodiments the method comprises administering a compound, including one of the compounds described herein, to a subject in need thereof. In some embodied methods a plurality of compounds according the present disclosure are administered simultaneously or in a predetermined sequence.

There are also provided processes for the preparation of a non-peptide proteasome inhibitor according to the present disclosure. For example, in some embodiments, the present disclosure provides processes for the preparation of a compound of formula (I), pharmaceutically acceptable salt, solvate, or physiologically functional derivative thereof.

Additionally, the present disclosure provides uses of a compound of formula (I), a salt, a solvate, or physiological derivative thereof in the preparation or manufacture of a drug and/or medicine, especially a medicine for the treatment of cancer in a mammal. In some embodiments, the cancer is a solid cancer.

Proteasome inhibitors according to the present disclosure were discovered via a virtual screening and medicinal chemistry approach. The compound of the following formula, for example,

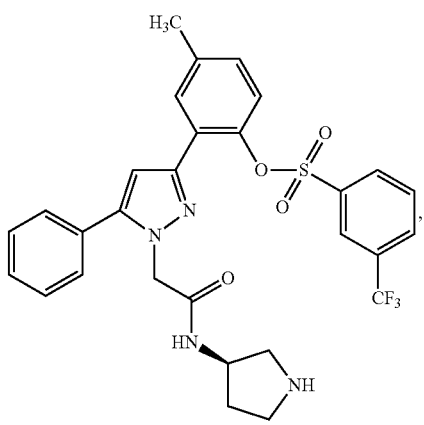 [SMILES: Cc1ccc(OS(=O)(=O)c2cccc(C(F)(F)F)c2)c(-c2cc(-c3ccccc3)n(CC(=O)N[C@@H]3CCNC3)n2)c1]

(also referred to herein as "G4-1"), targets both β5 and β5i and is highly effectively in suppressing tumor growth in a mouse xenograft model of prostate cancer. Furthermore, G4-1 is equally effective in killing both parental cells and model cell lines with acquired resistance to bortezomib or carfilzomib.

G4-1 was developed by a virtual screen of about 340,000 small molecules against the chymotrypsin-like (CT-L) activity conferring subunit of the proteasome followed by in vitro screening and subsequent optimization. Unlike carfilzomib and bortezomib, which contain linear peptide backbones and are metabolized rapidly, G4-1 shows excellent in vitro metabolic stability.

Furthermore, G4-1 is highly effective in suppressing tumor growth with no apparent toxicity in vivo. In addition, the effectiveness of G4-1 as an anticancer agent is not reduced by prior resistance to bortezomib or carfilzomib. Taken together, these results indicate that G4-1 is a metabolically stable proteasome inhibitor with a non-peptide scaffold that provides a new therapeutic option for multiple myeloma patients refractory to bortezomib or carfilzomib as well as for patients with solid cancers.

In some embodiments, the present disclosure provides non-peptide proteasome inhibitors that suppress tumor growth.

In some embodiments, the present disclosure provides methods for treating a subject with solid cancer(s) by administering to the subject an effective amount of at least one non-peptide proteasome inhibitor.

In some embodiments, the presently-disclosed subject matter provides a non-peptide proteasome inhibitor comprising at least one pyrazole. In certain embodiments, the present disclosure is directed to reversible non-peptide proteasome inhibitors.

In some embodiments, the presently-disclosed subject matter provides a method of inhibiting a proteasome in a cell, which involves administering an effective amount of a compound of formula (I) to the cell. In some embodiments, administering the compound to the cell leads to apoptosis of the cell. The cell can be, for example, a cancer cell.

In certain embodiments, the present disclosure provides a method of treating a disease, wherein the method comprises administering to a subject at least one non-peptide proteasome inhibitor, wherein the non-peptide proteasome inhibitor comprises at least one pyrazole.

In certain embodiments, the present disclosure provides a method of treating a disease, wherein the method comprises administering to a subject an effective amount of a pharmaceutical composition containing at least one compound according to formula (I).

In some embodiments, the present disclosure is directed to a pharmaceutical composition comprising at least one non-peptide proteasome inhibitor, wherein the proteasome inhibitor includes at least one pyrazole.

In some embodiments, the present disclosure is directed to a pharmaceutical composition comprising at least one compound according to formula (I).

In some embodiments, the present disclosure teaches a method of synthesizing a non-peptide proteasome inhibitor comprising at least one pyrazole.

In certain embodiments, the subject matter of the present disclosure includes a compound of formula (I), a pharmaceutically acceptable salt, solvate, or physiologically functional derivative thereof.

Further, the present disclosure provides, in certain embodiments, a method of treating a disease in a subject comprising the administration of an effective amount of a pharmaceutical composition containing a non-peptide protease inhibitor, a pharmaceutically acceptable salt, solvate or physiologically functional derivative thereof and pharmaceutically acceptable excipient to the subject.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Virtual Screening

Structure-based virtual screening was performed following a procedure reported previously by the present inventors.[23] Briefly, the conformation of proteasomes for virtual screening was selected from the molecular dynamics trajectory of recently built homology model in complex with newly discovered highly potent peptide compounds.[24] On the basis of favorable binding energy and optimal accommodation of the known inhibitors at the active site, the protein conformation at 341 ps was selected for the final screening. After docking 345 447 compounds included in the University of Cincinnati library, 288 compounds for the experimental validation were selected based on consensus scoring, force field based energy scoring functions (MM-PBSA and MM-GBSA and manual visualization of binding modes). Out of 288 compounds tested, 19 compounds were found to be active at 5/4M in a CT-L activity assay using the IP (more details in the following section). Among these compounds, G4 was found to potently inhibit the CT-L activity of the CP and IP. G4-1, an analogue of G-4, was prepared following a synthetic scheme described in FIG. 2D and HPLC purification with purity greater than 98%.

Screening Via In Vitro Proteasome Kinetics.

Compounds were dissolved in DMSO and were used at a concentration of 5 μM. The stock concentrations of each compound were adjusted to make total DMSO percentage (v/v) less than 1% in the final reaction solution. 20S human immunoproteasomes (IP) and constitutive proteasomes (CP) purchased from Boston Biochem were diluted to 1× assay buffer condition (20 mM Tris/Cl, pH 8.0, 0.5 mM EDTA, 0.035% SDS). 1, 2 Compounds were pre-incubated with 50 ng/well of IP or CP in a 96-well plate at room temperature for 90 min. 100 μM of Suc-LLVY-AMC (Sigma) in 1× assay buffer was then added to the wells. Fluorescent signals from hydrolyzed AMC (Ex: 360 nm, Em: 460 nm) were recorded once per min up to 90 min. The DMSO treated vehicle control was used to convert the initial velocities (RFU/min) to the percent CT-L activity. The data were collected from three individually performed experiments, and then the mean, standard deviation values were calculated.

Enzyme Kinetics Assays.

Initially, purified 20S human proteasomes (CP and IP, R&D Systems) were used to assess the in vitro inhibition of proteasome catalytic activities by G4 and its analogs. In the 96-well format assays involving a 100/4 L total volume, 20S proteasomes (0.5/4 g/mL) were incubated with G4, its analogs, or reference compounds (e.g., carfilzomib) in assay buffer (20 mM Tris-HCl, 0.5 mM EDTA, 0.035% SDS) for 30 min at room temperature. Reactions were initiated by the addition of individual subunit-selective fluorogenic substrates containing the AMC (7-amino-4-methylcoumarin) group. The following substrates were used: for /31 activity, Ac-nLPnLD-AMC (100/4M); for /32 and /32i activity, Boc-LRR-AMC (200/4M); for /35 activity, Ac-WLA-AMC (20/4M); for /31i activity, Ac-PAL-AMC (100/4M); for /35i activity, Ac-ANW-AMC (100/4M). The fluorescence of liberated AMC was measured over a period of 90 min at room temperature using excitation and emission wavelengths of 360 and 460 nm on a SpectraMax M5 fluorescence plate reader (Molecular Devices).

In separate experiments, cytosolic extracts of RPMI-8226 or BxPC-3 cells were prepared according to the method of Kisselev and Goldberg[25] and used in place of purified proteasomes. The fluorescence from liberated AMC of the subunit-selective probe substrates was measured as described above.

Jump Dilution Reversibility Assay.

In further investigation of the mode of proteasome inhibition by G4-1, a dilution assay was performed following a procedure previously reported.[26] Briefly, RPMI 8226 cell lysates containing 30/4 g of total protein were incubated with G4-1 (10/4M) in 20S proteasome assay buffer for 30 min at room temperature. Lysates treated with G4-1 were subsequently transferred to a semimicrocuvette, and the baseline proteasome activity was determined by measuring the hydrolysis rate of Suc-LLVY-AMC. After establishment of the baseline, lysates treated with G4-1 were rapidly mixed with the 20S proteasome assay buffer, yielding 25-fold dilution. Following this 25-fold dilution from 10 to 0.4/4M G4-1, the hydrolysis of Suc-LLVY-AMC was again monitored over approximately 30 min.

Cell Culture.

Human cancer cell lines BxPC-3, H358, H-23, LNCaP, Panc-1, and RPMI 8226 were obtained from the ATCC (American Type Culture Collection) and maintained in the ATCC-recommended media, DMEM or RPMI 1640 supplemented with 10% fetal bovine serum (from GIBCO, Celi-Gro, and Atlanta Biologicals). BxPC-3 cells with acquired resistance to bortezomib or carfilzomib were established by growing them in the presence of stepwise in-creasing concentrations of the respective drug over a period of approximately 6 months. In order to determine the extent of drug resistance, cytotoxicity assays were performed using BxPC-3 sublines adapted to 60 nM bortezomib and 200 nM carfilzomib, respectively.

Measurement of Cytotoxic Effects of G4 and its Analogs.

The cytotoxic effects of G4 and its analogs were determined using CellTiter Glo assay or CellTiter 96 Aqueous One Solution Cell Proliferation assay (Promega). Adherent cells (Panc-1, LNCaP, BxPC-3, bortezomib- or carfilzomib-resistant BxPC-3 sublines) growing in log phase were plated at 7000-10000 cells per well. RPMI 8226 cells growing in suspension were collected by centrifugation and plated at 10 000 cells per well. Twenty-four hours after plating, media containing the test compounds were added to each well to deliver the intended final concentration. After 72 h, the cell viability was determined using the assay protocol recommended by the manufacturers. The resulting signals were quantified using a Veritas microplate luminometer or a SpectraMax M5 microplate spectrophotometer (Molecular Devices).

Microsomal Stability Assay.

The metabolic stability profiles of G4-1 and reference compounds (carfilzomib and bortezomib) were assessed by monitoring the disappearance of the test compounds in the presence of liver microsomes. A typical incubation mixture (100 sL total volume) for metabolic stability studies contained 1 sM test compounds, 0.5 mg/mL microsomal protein (pooled Balb/c mouse liver microsomes prepared in-house or BD UltraPool human liver microsomes), 100 mM Tris-HCl buffer (pH 7.4), and NADPH-generating system (5 mM isocitric acid, 0.2 unit/mL isocitric acid dehydrogenase, 5 mM magnesium chloride, 1 mM NADP$^+$). After preincubation at 37° C. for 5 min, the reactions were started by addition of NADP$^+$ and further incubated for another 0, 5, 10, 20 min. For control experiments, NADPH and/or liver microsomes were omitted from these incubations. The reactions were terminated by adding 100 sL of ice-cold acetonitrile containing phenytoin (1 sM) as internal standard and keeping on ice for 30 min, followed by centrifugation at 16 100 g for 15 min to obtain the supernatant. Aliquots (5 sL) were then analyzed for substrate disappearance using liquid chromatography-tandem mass spectrometry (Agilent 1200 HPLC instrument interfaced with Applied Biosystems Qtrap 3200) equipped with an electrospray ion source.

In Vivo Efficacy Assay.

Six-week-old male BALB/c athymic nude mice (purchased from Orient Bio Inc., SungNam, Republic of Korea) were maintained in accordance with the National Institute of Toxicological Research of the Korea Food and Drug Administration guidelines as well as the regulations for the care and use of laboratory animals of the animal ethics committee of the Konyang University. LNCaP cells ($2\times10^6$ cells/50 sL) were subcutaneously implanted into each animal. After the xenograft tumors had grown to a size of '–100 mm$^3$, mice (n=5/group) were dosed intraperitoneally twice a week for 4 weeks with G4-1 (5 mg/kg), carfilzomib (5 mg/kg), or vehicle only (8% DMSO in HP-Beta-CD and citrate). Tumor volumes (calculated using the following formula, (width)$^2\times$length/2) and body weights were measured every 4 days during the experimental period. At the end of the experimental period (at day 30), mice were euthanized by cervical dislocation and tumors were isolated and weighed.

Results and Discussion

Screening of a Small Molecule Library Against the CT-L Activity of Proteasomes.

The majority of currently available proteasome inhibitors including bortezomib and carfilzomib are small peptides with an electrophilic warhead.[27] These electro-philic warheads such as boronates, epoxyketones, /3-lactones, and vinyl sulfones directly target the hydroxyl nucleophile of the N-terminal threonine in the active site, blocking the proteolytic activity of proteasome via covalent modifications.[28] Although the combination of a peptide backbone with an electrophilic pharmacophore can provide a relatively easy route to proteasomal inhibition, it may suffer from poor metabolic stability and side effects.[18,20,29,30] To circumvent these concerns, increased efforts have been made recently to generate CT-L activity targeting peptide or non-peptide, reversible proteasome inhibitors.[31-37] However, no further development has been made to date, mainly because of low proteasome inhibitory potency or poor in vivo efficacy of these compounds.

In the current study, the present inventors employed a stepwise screening strategy to identify non-peptide proteasome inhibitors lacking reactive warheads with improved potency and efficacy against proteasomes (FIG. 2A). Given that the CT-L activity-conferring /35 and /35i subunits share a high degree of structural homology at the active sites,[38] the present inventors performed a virtual screening of a library of 345 447 small molecules (provided by University of Cincinnati Drug Discovery Center) against the /35i subunit following a procedure described by us[23] and selected 288 compounds based on their predicted fit into the active site of /35i.

These selected 288 compounds were then tested for their ability to inhibit the CT-L activity of proteasomes, and subsequently G4 was identified as a lead inhibitor (FIG. 2A). Since only a limited amount of G4 was available from the library, the present inventors synthesized G4 following the scheme described in FIG. 2B. Using this synthetic G4 compound, the present inventors found that G4 preferentially inhibits the CT-L activity-conferring /31i and /35//35i and C-L activity responsible /31 but not /32//32i subunits which are responsible for T-L activity (FIG. 2C). Consistent with its ability to inhibit the proteasome activity in vitro, G4 effectively induced cancer cell death in the low micromolar range (IC50 $\cong$7 sM) (FIG. 2D).

Investigation of the G4 Chemical Space.

Figure 3A:
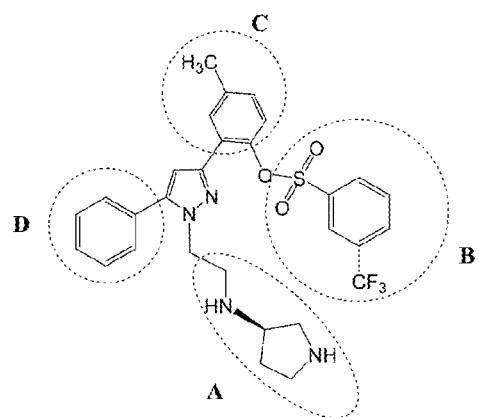
FIG. 3A illustrates structural features of G4 that are suitable for modification.
Figure 3B:
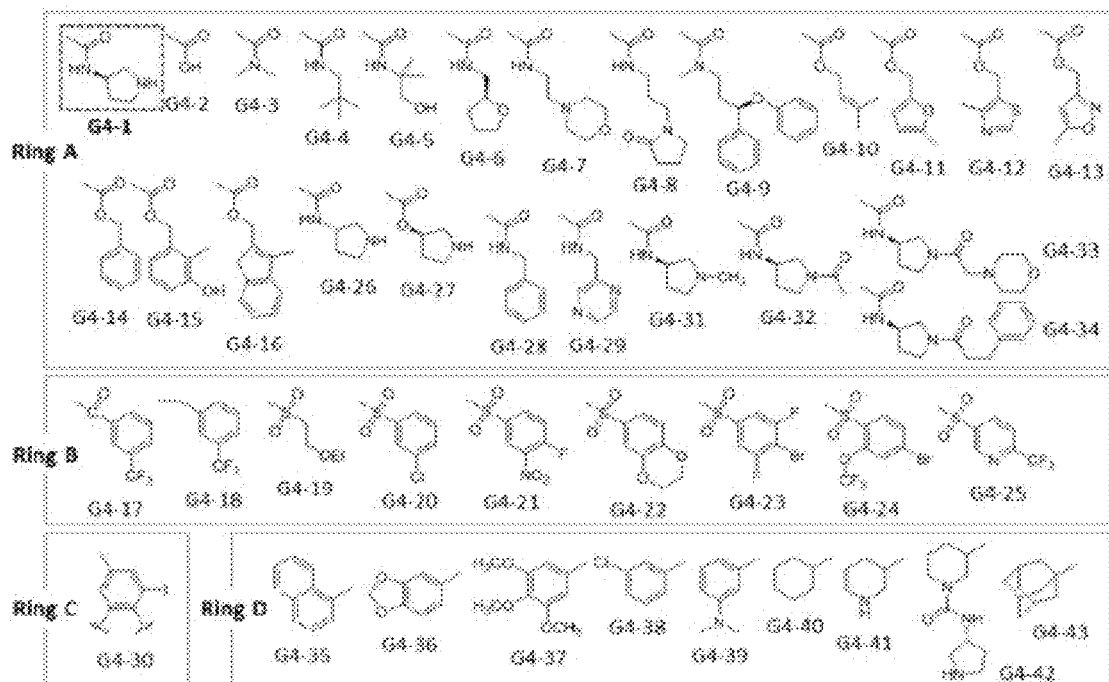
FIG. 3B provides G4 derivatives, illustrating modifications relative to FIG. 3A.

To probe structure-activity-relationship of G4 compound, the present inventors created a library of G4 analogs modified at rings A-D following synthetic procedures similar to that described in FIG. 2B (FIG. 3A-B; see below for modified synthetic schemes) and measured their potencies against the CT-L activity of purified proteasomes. The enzyme kinetics studies demonstrated that modifications at rings A and B have significant impacts on inhibitory activity, G4-1 being one of the most potent inhibitors (FIG. 3D-3F). In comparison, modifications at the ring D had little impact on the activity of G4. Interestingly, while most of these G4 derivatives inhibit the CT-L activity of proteasome, some such as G4-16 and G4-21 activated the CT-L activity of proteasomes, up to 200% at 10 sM (FIG. 3D). The mechanism by which these compounds enhance the CT-L activity of proteasome is unclear at this time. While further target validation study is needed, the initial studies using these G4-1 derivatives showed an apparent correlation between the proteasome inhibitory activity and the anticancer effects of pyrazole-based G4 analogs, indicating that proteasome inhibition is likely to mediate the cytotoxic effects of G4 and G4-1 (FIG. 3G).

Figure 3C:
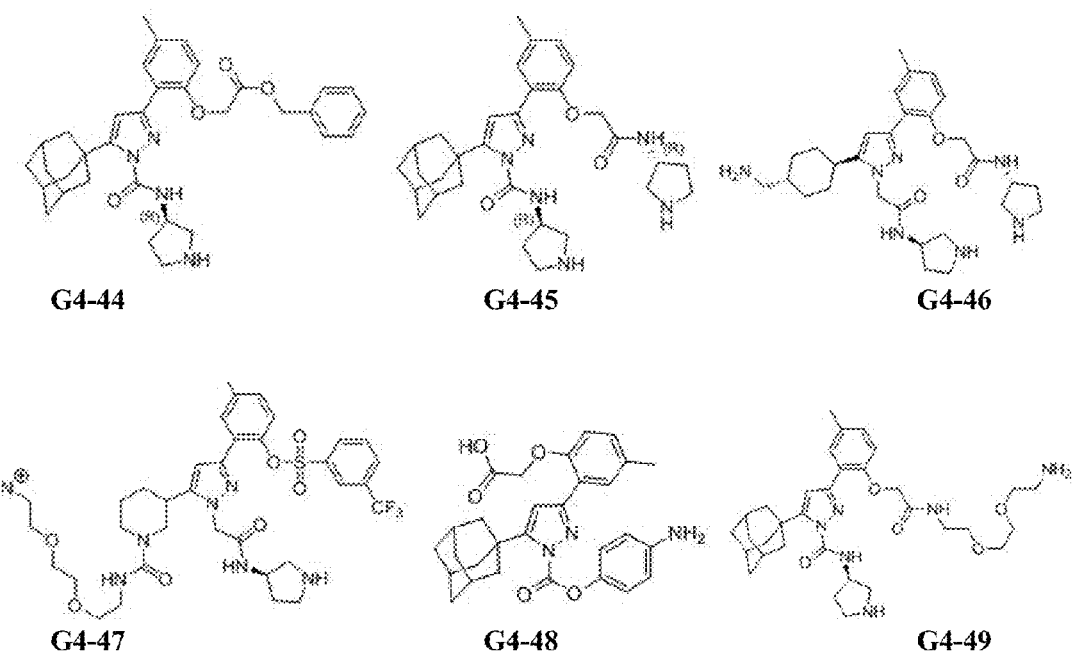
FIG. 3C depicts additional G4 derivatives.
Figure 3D:
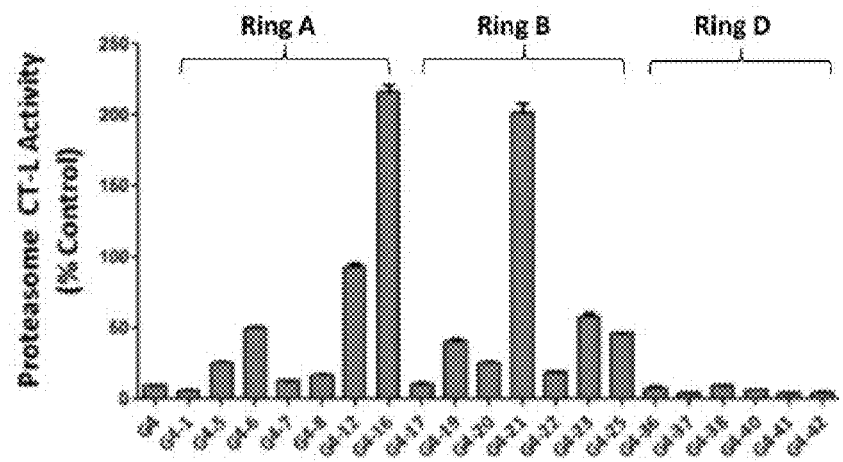
FIG. 3D illustrates inhibitory activity of selected G4 derivatives toward the CT-L activity of the proteasome.
Figure 3H:
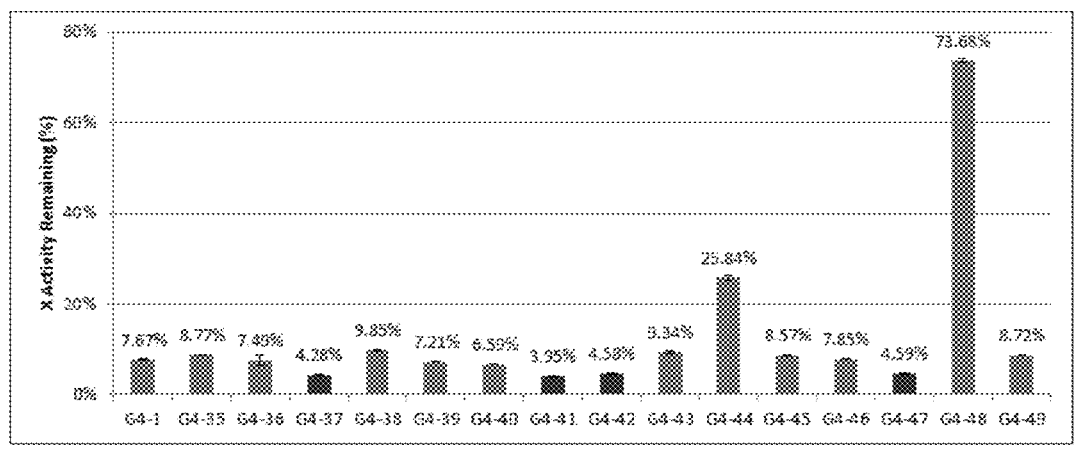
FIG. 3H illustrates inhibitory activity of selected G4 derivatives against more clinically relevant proteasome catalytic subunit X.

With further reference to FIGS. 3C and 3H, Compounds hydrophobic or water-friendly groups at R1 and/or R2 positions were prepared. Inhibitory activity assay against more clinically relevant proteasome catalytic subunit X showed that positively charged groups at R1 and R2 positions are favored for the inhibition of proteasome catalytic subunit X.

Figure 4A:
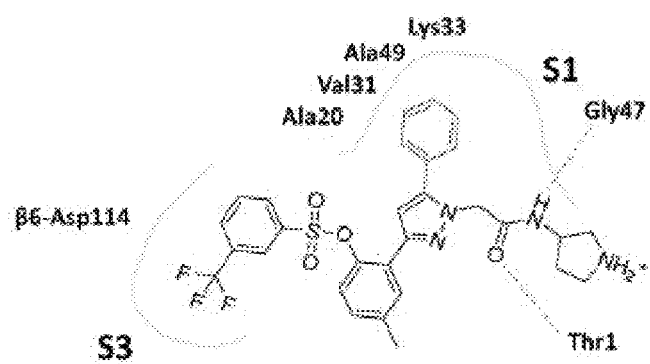
FIGS. 4A and 4B illustrate the predicted 05 binding mode of G4-1 and bortezomib generated by Autodock Vina.[39]
Figure 4B:
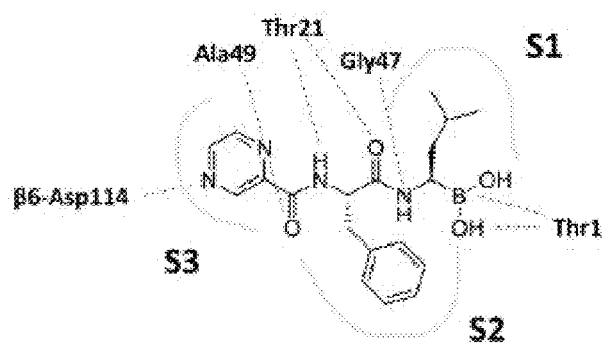

The present inventors next further investigated the structure-activity relationship (SAR) by docking simulation of G4-1 to the /35 subunit of the proteasome. The docking studies suggest that the improved activity of G4-1 over G-4 may be attributed to hydrogen bonds created by the introduction of an amide linkage at the ring A (FIG. 4A). Ring B is predicted to occupy the S3 subsite located at the interface between /35 and /36 subunits. Ring D of G4-1 is predicted to occupy the S1 subsite but not as deeply and fully as the Leu side chain of bortezomib (FIG. 4B). Overall, G4-1 is predicted to occupy only two subsites, as compared to three for bortezomib (FIG. 4B), and this predicted difference may be exploited to further improve inhibitory potency of G4-1.

G4-1 as a Lead Proteasome Inhibitor.

Given its improved inhibitory potency against the CT-L activity of purified proteasomes and additional optimization potential (due to the amide linkage at the ring A), as compared to G4, the present inventors decided to further characterize G4-1 as a lead non-peptide proteasome inhibitor. It should be mentioned that although compounds G4-40, G4-41, and G4-42 showed the ability to potently inhibit in vitro CT-L activity (FIG. 3D), the present inventors found that G-40, G4-41, and G4-42 were less potent or noncytotoxic in the initial cell viability assays, compared to G4-1 (FIG. 3F), thus justifying the selection of G4-1 for further in vitro and in vivo studies. The present inventors first tested the ability of G4-1 to inhibit the activity of cellular proteasomes present in cell extracts, other than just purified proteasomes. As shown in FIG. 5A, G4-1 was able to effectively inhibit the proteasomal CT-L and C-L activities of cell extracts. Similar to G4, G4-1 showed no activity against the T-L activity of cell extracts.

Given that the majority of currently available proteasome inhibitors, which contain peptide backbones, are prone to rapid in vivo inactivation,[31-33,36] the present inventors next examined whether the pyrazole scaffold-based proteasome inhibitor G4-1 is metabolically more stable than those peptide-based drugs. Excitingly, G4-1 demonstrated excellent metabolic stability profiles in mouse and human liver microsomes, as compared to carfilzomib and bortezomib (FIG. 5B). These results indicate that G4-1 is likely to have much improved in vivo stability compared to carfilzomib and bortezomib, which are known to undergo rapid metabolic inactivation.[18,21,40]

Next, the present inventors investigated the mode of proteasome inhibition by G4-1 using a jump dilution reversibility assay previously reported.[26] Preincubation of RPMI 8226 cell extracts with G4-1 for 30 min resulted in a nearly complete inhibition of proteasomal activity. However, after 25-fold dilution, the reaction rate increased exponentially with an inhibitor dissociation half-life of approximately 3.2 min (FIG. 5C), indicating the reversibility of G4-1/proteasome interaction. As expected, G4-1 showed a good anticancer activity against a variety of cancer cell lines including LNCaP prostate cancer cells (FIG. 5D). Interestingly, the anticancer effect of G4-1 was not negatively impacted by acquired resistance to bortezomib or carfilzomib in cell line models (FIG. 5E), which was generated by continuous drug exposure with stepwise increases in concentration (FIG. 5F).

In Vivo Anticancer Activity of G4-1.

Lastly, the Present Inventors Investigated the in vivo anticancer efficacy of G4-1 using a xenograft mouse model. Given that one of important goals in the area of proteasome inhibitor therapy is to expand therapeutic benefits to patients with solid cancers, the present inventors used a solid cancer xenograft model of human prostate LNCaP cancer cell line following a procedure the present inventors previously reported.[6] As shown in FIG. 6A-C, G4-1 effectively suppressed tumor growth in vivo without apparent systemic toxicity in mice (for images of mice treated with G4-1, see FIG. 6E). Unlike mice treated with carfilzomib which resulted in weight loss, mice treated with G4-1 maintained normal weight gain over the course of treatment (FIG. 6D).

Conclusions

The present inventors have successfully developed a group of non-peptide, reversible proteasome inhibitors, including G4-1. This inhibitor utilizes a pyrazole scaffold and does not rely on an electrophilic warhead to mediate proteasome inhibition. In addition to its novel scaffold, G4-1 represents an important advance due to its effectiveness in models of proteasome inhibitor resistance and metabolic stability. This is notable, as MM patients who are initially responsive to currently FDA-approved proteasome inhibitors almost inevitably develop resistance to those drugs. Therefore, G4-1 provides an opportunity for an additional option for these refractory MM patients. Multiple clinical trials clearly demonstrated that the clinically approved proteasome inhibitors carfilzomib and bortezomib lack utility in the treatment of solid tumors due to their rapid metabolism, irreversible inhibition, sensitivity to resistance, and dose-limiting toxic-ities.[18,20,22,41,42]

Synthesis of Compounds

Synthesis of G4.

G4 was synthesized following a procedure described below and set forth in FIG. 2B.

Compound 2: Hydrazine (0.15 mL, 4.713 mmol) was added to a solution of 1-(2-Hydroxy-5-methylphenyl)-3-phenyl-1, 3-propanedione (1 g, 3.928 mmol) in ethanol (10 mL). The mixture was refluxed with stirring for 1 h. The mixture was cooled to room temperature. The solvent was evaporated to dryness. The formed precipitate was taken in ethyl acetate (30 mL), washed with brine (3×30 mL), and dried over anhydrous sodium sulfate. The solvent was evaporated and the solid residue was recrystallized from hot ethanol. Compound 2 was obtained as yellow solid (955 mg, 97%). $^1$H NMR (CDCl$_3$, 500 MHz) δ 10.62 (bs, 1H), 10.34 (bs, 1H), 7.61 (d, 2H, J=9.5 Hz), 7.49-7.41 (m, 4H), 7.05 (d, 1H, J=10.0 HZ), 6.96 (d, 1H, J=8.0 Hz), 6.90 (s, 1H), 2.34 (s, 3H)

Compound 3: Benzyl 2-bromoacetate (0.14 mL, 0.909 mmol) was added to a solution of Compound 2 (455 mg, 1.818 mmol) in NMP (10 mL). The resulting solution was heated at about 60-70° C. for 1 hours. The crude product was purified by column chromatography on silica gel using hexane-ethyl acetate mixture to afford compound 3 as a white solid (167 mg, 46%). $^1$H NMR (CDCl$_3$, 500 MHz) δ 10.38 (s, 1H), 7.44-7.28 (m, 11H), 7.039 (d, 1H, J=8.0 Hz), 6.93 (d, 1H, J=8.0 Hz), 6.70 (s, 1H), 5.18 (s, 2H), 4.92 (s, 2H), 2.31 (s, 3H)

Compound 4: Lithium aluminum hydride (29 mg, 0.764 mmol) was added to a solution of Compound 3 (100 mg, 0.251 mmol) in anhydrous THF (10 mL). The mixture was stirred at room temperature under nitrogen atmosphere for 2 h. After that period the mixture was carefully poured into ice water (30 mL) and acidified with 1M HCl at pH 2-3. The crude product was extracted by ethyl acetate (3×30 mL), dried over anhydrous sodium sulfate. The solvent was evaporated and purified by column chromatography on silica gel using hexane-ethyl acetate mixture to afford compound 4 as a white solid (60 mg, 80%).$^{1H}$ NMR (CDCl$_3$, 500 MHz) δ10.48 (s, 1H), 7-53-7.42 (m, 5H), 7.38 (s, 1H), 7.039 (d, 1H, J=8.0 Hz), 6.939 (d, 1H, J =8.0 Hz), 6.68 (s, 1H), 4.32-4.24 (m, 2H), 4.09-4.08 (m, 2H), 2.33 (s, 3H), 1.89 (bs, 1H)

Compound 5: Triethylamine (0.014 mL, 0.102 mmol) was added to a solution of compound 4 (20 mg, 0.068 mmol) and 4-Toluensulfonyl chloride (14 mg, 0.075 mmol) in dichloromethane (1 mL). The resulting solution was stirred at rt for overnight. The reaction mixture was concentrated under reduced pressure. The crude product was purified by column chromatography on silica gel using hexane-ethyl acetate mixture to afford compound 5 as a white solid (13 mg, 43%). $^1$H NMR (CDCl$_3$, 500 MHz) δ10.02 (s, 1H), 7.52-7.45 (m, 7H), 7.31 (s, 1H), 7.06-7.03 (m, 3H), 6.89 (d, 1H, J=8.0 Hz), 6.53 (s, 1H), 4.43 (t, 2H, J=5.0 Hz), 4.29 (t, 2H, J=5.0 Hz), 2.33 (s, 3H), 2.07 (s, 3H)

Compound 6: Triethylamine (0.008 mL, 0.06 mmol) was added to a solution of compound 5 (9 mg, 0.02 mmol) and 3-(Trifluoromethyl)benzenesulfonyl chloride (0.006 ml, 0.04 mmol) in dichloromethane (1 mL). The resulting solution was stirred at rt for 6 h. The reaction mixture was concentrated under reduced pressure. The crude product was purified by column chromatography on silica gel using hexane-ethyl acetate mixture to afford compound 6 as a white solid (12 mg, 91%). $^1$H NMR (CDCl$_3$, 500 MHz) δ7.86 (s, 1H), 7.737 (d, 2H, J=8.0 Hz), 7.57 (d, 2H, J=8.5), 7.49-7.36 (m, 7H) 7.29 (d, 1H, J=8.5 Hz), 7.187.14 (m, 3H), 6.55 (s, 1H), 4.42 (t, 2H, J=5.5 Hz), 4.24 (t, 2H, J=5.5 Hz), 2.36 (s, 3H), 2.26 (s, 3H)

Compound 7: (R)-(+)-1-Boc-3-aminopyrrolidine (7 mg, 0.0364 mmol) was added to a solution of compound 6 (12 mg, 0.0182 mmol) and potassium carbonate (0.005 mg, 0.0364 mmol) in DMF (0.5 mL). The resulting solution was stirred at rt for 2 h. The reaction mixture was concentrated under reduced pressure. The crude product was purified by column chromatography on silica gel using hexane-ethyl acetate mixture to afford compound 7 as a white solid (8 mg, 66%). $^1$H NMR (CDCl$_3$, 500 MHz) δ7.92 (s, 1H), 7.78-7.76 (m, 2H), 7.57-7.41 (m, 7H), 7.23 (m, 1H), 7.13-7.11 (m, 1H), 6.58 (s, 1H) 4.17 (m, 2H), 3.89 (m, 1H), 3.64-3.22 (m, 6H), 3.03 (m, 2H), 2.37 (s, 3H)

G4: Trifluoroacetic acid (0.5 mL) was added to a solution of Compound 7 (8 mg, 0.0119 mmol) in dichloromethane (1 mL). The resulting solution was stirred at rt for 1 h. The reaction mixture was concentrated under reduced pressure. The crude product was purified by column chromatography on silica gel using dichloromethane-methanol mixture to afford G4 as a semi solid (5 mg, 73%). $^1$H NMR (CDCl$_3$, 500 MHz) δ10.69 (bs, 1H), 10.11 (bs, 1H), 7.96-7.78 (m, 3H), 7.59-7.35 (m, 7H), 7.13-7.09 (m, 2H), 6.96 (d, 1H, J=8.5 Hz), 6.45 (s, 1H), 4.60 (m, 2H), 4.23 (m, 1H), 3.85 (m, 2H), 3.61 (m, 4), 2.37 (m, 5H), $[\alpha]_d^{25}$=+1.2 (c=0.14, CHCl$_3$)

Synthesis of G4-1.

G4-1 was synthesized by the following procedure, which is further described below.

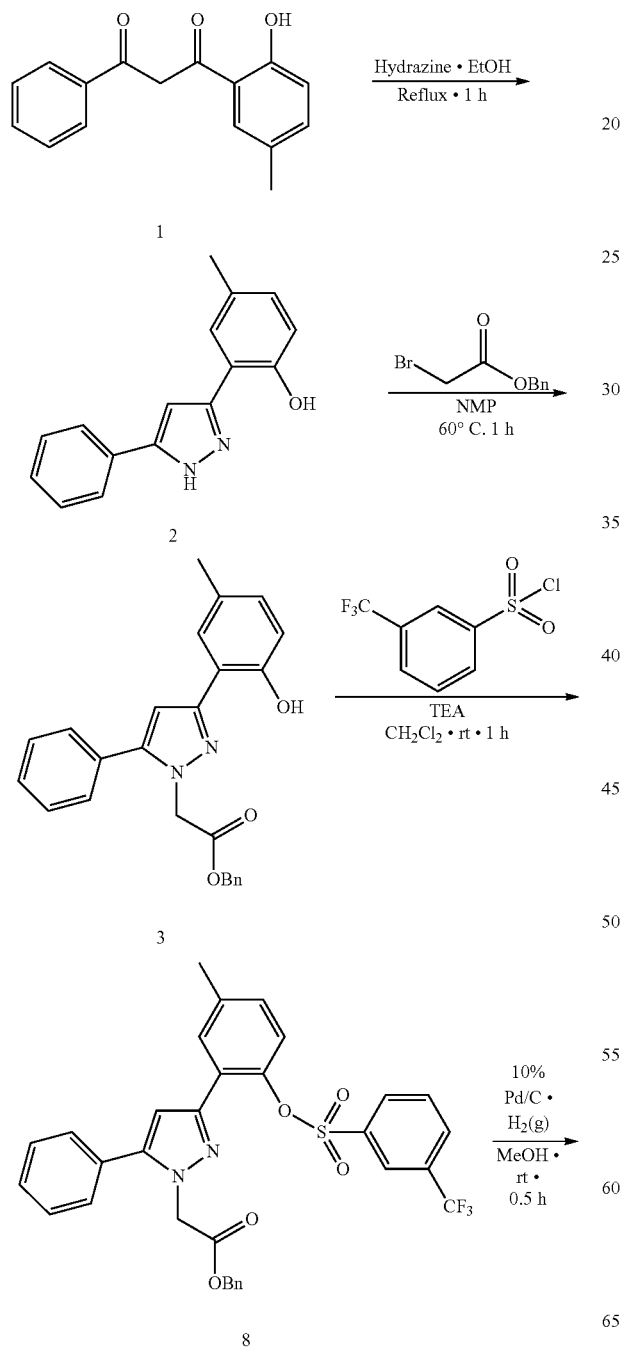

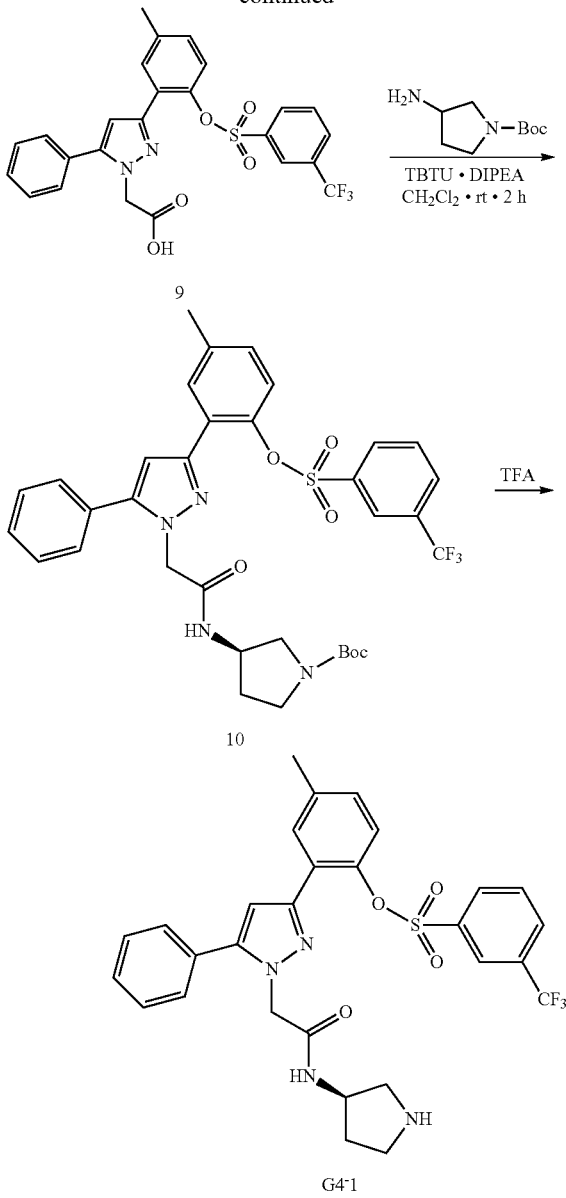

Compound 8: Triethylamine (0.02 mL, 0.139 mmol) was added to a solution of compound 3 (37 mg, 0.0928 mmol) and 3-(Trifluoromethyl)benzenesulfonyl chloride (0.016 mL, 0.102 mmol) in dichloromethane (1 mL). The resulting solution was stirred at rt for 1 h. The reaction mixture was concentrated under reduced pressure. The crude product was purified by column chromatography on silica gel using hexane-ethyl acetate mixture to afford compound 8 as a white solid (50 mg, 89%). $^{1H}$ NMR (CDCl$_3$, 500 MHz) δ7.89 (s, 1H), 7.72 d, 2H, J=7.0 Hz), 7.56 (s, 1H), 7.46-7.32 (m, 12H), 7.15 (d, 1H, J=8.0 Hz), 6.62 (s, 1H), 5.20 (s, 2H), 4.85 (s, 2H), 2.34 (s, 3H)

Compound 9: To a solution of compound 8 (40 mg, 0.0659 mmol) in methanol (2 mL) was added 10% Pd/C (10 mg) and the reaction vessel purged with H$_2$ gas. The reaction mixture was stirred under H$_2$ atmosphere (H$_2$ balloon) for 0.5 h. Excess H$_2$ was displaced by air and the catalyst was removed by filtration through Celite. The filtrate was concentrated under reduced pressure. Compound 9 as a semi solid (34 mg, 99%). ¹H NMR (CDCl₃, 500 MHz) δ 9.22 (bs, 1H), 7.81 (s, 1H), 7.71-7.67 (m, 2H), 7.477.33 (m, 8H), 7.16 (d, 1H, J=8.0 Hz), 6.48 (s, 1H), 4.87 (s, 2H), 2.27 (s, 3H)

Compound 10: N,N-Diisopropylethylamine (0.057 ml, 0.33 mmol) was added to a solution of compound 9 (24 mg, 0.0658 mmol), (R)-(+)-1-Boc-3-aminopyrrolidine (12 mg, 0 0658 mmol), and 0-(benzotriazol-1-yl)-N,N,N',N'-tetramethyluronium tetrafluorobotate (32 mg, 0.099 mmol) in dichloromethane (2 mL). The resulting solution was stirred at rt for 2 h. The reaction mixture was concentrated under reduced pressure. The crude product was purified by column chromatography on silica gel using hexane-ethyl acetate mixture to afford compound 10 as a white solid (40 mg, 89%). ¹H NMR (CDCl₃, 500 MHz) δ7.99 (s, 1H), 7.88-7.84 (m, 2H), 7.58-7.37 (m, 7H), 7.24 (d, 1H, J=8.0 Hz), 6.97-6.90 (m, 1H), 6.72 (s, 1H), 6.42 (m, 1H), 4.80 (s, 2H), 4.45-4.43 (m, 1H), 3.63-3.59 (m, 1H), 3.35-3.31 (m, 2H), 3.04 (m, 1H), 2.39 (s, 3H), 2.12-2.09 (m, 1H), 1.76 (m, 1H)1.37 (s, 9H)

G4-1: Trifluoroacetic acid (0.5 mL) was added to a solution of compound 10 (20 mg, 0.0292 mmol) in dichloromethane (1 mL). The resulting solution was stirred at rt for 0.5 h. The reaction mixture was concentrated under reduced pressure. The crude product was purified by column chromatography on silica gel using dichloromethane-methanol mixture to afford G4-1 as a semi solid (12 mg, 70%). G4-1 was further purified by HPLC to yield G4-1 with purity greater than 98.5%. ¹H NMR (CDCl₃, 500 MHz) δ9.22 (bs, 1H), 9.01 (bs, 1H), 8.00 (s, 1H), 7.88-7.81 (m, 3H), 7.57-7.39 (m, 7H), 7.13 (d, 1H, J=8.0 Hz), 7.11 (d, 1H, J=8.0 Hz), 6.55 (s, 1H), 4.81 (s, 2H), 4.51 (m, 1H), 3.48-3.29 (m, 4H), 2.34-2.27 (m, 4H), 2.05 (m, 1H); MS (ESI): M+H⁺, $C_{29}H_{28}F_3N_4O_4S$, Calcd. 585.1778. found 585.1779. $[\alpha]_D^{25}=-11.5$ (C=0.23, CHCl₃)

G4-1 derivatives were synthesized following a procedure used for the synthesis of G4-1 with exception of using different starting materials. Representative nmr and mass data for some G4-1 derivatives (G4-2-G4-13) are provided below.

G4-2: ¹H NMR (CDCl₃, 500 MHz) δ7.83 (s, 1H), 7.74 (d, 2H, J=7.5 Hz), 7.46-7.15 (m, 9H), 6.51 (s, 1H), 4.83 (s, 2H), 2.31 (s, 3H)

G4-3: ¹H NMR (CDCl₃, 500 MHz) δ7.84 (s, 1H), 7.75-7.71 (m, 2), 7.53-7.41 (m, 7H), 7.44 (d, 1H, J =8.0 Hz), 7.12 (d, 1H, J=8.0 Hz), 6.57 (s, 1H), 4.85 (s, 2H), 3.02 (s, 3H), 3.00 (s, 3H), 2.32 (s, 3H)); MS (MALDI-TOF): MH⁺, Calcd. for $C_{27}H_{25}F_3N_3O_4S$ 544.1. found 544.1.

G4-4: ¹H NMR (CDCl₃, 500 MHz) δ7.96 (s, 1H), 7.85-7.80 (m, 2H), 7.61 (s, 1H), 7.54-7.38 (m, 6H), 7.13-7.10 (m, 2H), 6.73 (s, 1H), 6.44 (m, 1H), 4.78 (s, 2H), 3.08 (d, 2H, J=8.5 Hz), 2.37 (s, 3H), 0.82 (s, 3H); MS (MALDI-TOF): MH⁺, Calcd. 586.2 for $C_{30}H_{31}F_3N_3O_4S$. found 586.2.

G4-5: ¹H NMR (CDCl₃, 500 MHz) δ7.98 (s, 1H), 7.87-7.82 (m, 2H), 7.59-7.46 (m, 5H), 7.99 (d, 2H, J=8.0 Hz), 7.12 (d, 1H, J=7.5 Hz), 7.03 (d, 1H, J=7.5 Hz), 6.70 (s, 1H), 6.39 (s, 1H), 4.72 (s, 2H), 3.54 (s, 2H), 2.38 (s, 3H), 1.25 (s, 6); MS (MALDI-TOF): MH⁺, Calcd. for $C_{29}H_{29}F_3N_3O_5S$ 588.2. found 588.2.

G4-6: ¹H NMR (CDCl₃, 500 MHz) δ7.94 (s, 1H), 7.84-7.78 (m, 2H), 7.63 (s, 1H), 7.52-7.37 (m, 6H), 7.20-7.14 (m, 2H), 6.61 (m, 2H), 4.73 (s, 2H), 3.97-3.92 (m, 1H), 3.75-3.64 (m, 2H), 3.54-3.50 (m, 1H), 3.29-3.26 (m, 2H), 2.38 (s, 3H), 1.95-1.78 (m, 3H), 1.53-1.47 (m, 1H); MS (MALDI-TOF): MH⁺, Calcd. for 600.2. found 600.2.

G4-7: ¹H NMR (CDCl₃, 500 MHz) δ7.97 (s, 1H), 7.86-7.82 (m, 2H), 7.62 (s, 1H), 7.57-7.47 (m, 4H), 7.39 (d, 2H, J=8.0 Hz), 7.14 (d, 1H, J=8.0 Hz), 7.08 (d, 1H, J=8.0 Hz), 6.71 (s, 1H), 6.65 (s, 1H), 4.77 (s, 2H), 3.71-3.68 (m, 1H), 3.47-3.37 (m, 4H), 3.15-3.13 (m, 1H), 2.45-2.43 (m, 2H), 2.38 (s, 3H), 2.372.35 (m, 4H)

G4-8: ¹H NMR (CDCl₃, 500 MHz) δ7.92 (s, 1H), 7.86-7.79 (m, 2H), 7.62 (s, 1H), 7.55 (t, 1H, J=7.5 Hz), 7.46-7.41 (m, 5H), 7.13-7.05 (m, 2H), 6.91 (s, 1H), 6.61 (s, 1H), 4.74 (s, 2), 3.69-3.62 (m, 1H), 3.34-3.26 (m, 5H), 2.36-2.31 (m, 5H), 2.04-1.95 (m, 2H), 1.73-1.70 (m, 2H); MS (MALDI-TOF): MH⁺, Calcd. for $C_{32}H_{32}F_3N_4O_5S$ 641.2. found 642.2.

G4-9: ¹H NMR (CDCl₃, 500 MHz) δ7.85-7.83 (m, 1H), 7.74-7.67 (m, 2H), 7.54 (s, 1H), 7.48-7.23 (m, 12H), 7.12-7.08 (m, 2H), 6.94-6.89 (m, 1H), 6.76 (m, 1H), 6.58-6.49 (m, 2H), 5.16-5.14 (m, 1H), 4.82 (s, 2H), 3.63-3.53 (m, 2H), 2.98-2.93 (m, 3H), 2.33-2.27 (m, 6H), 2.17-2.12 (m, 2H); MS (MALDI-TOF): MH⁺, Calcd. for $C_{42}H_{38}F_3N_3O_5S$, 586.2. found 754.2.

G4-10: ¹H NMR (CDCl₃, 500 MHz) δ 7.87 (s, 1H), 7.75-7.71 (m, 2H), 7.61 (s, 1H), 7.55-7.34 (m, 7H), 7.15 (d, 1H, J=8.5 Hz), 6.59 (s, 1H), 5.33-5.30 (m, 1H), 4.84 (s, 2H), 4.66 (d, 2H, J=7.5 Hz), 2.34 (s, 3H), 1.76 (s, 3H), 1.70 (s, 3H); MS (MALDI-TOF): MK⁺, Calcd. for $C_{30}H_{30}F_3KN_3O_4S$. 623.2. found 623.2.

G4-11: ¹H NMR (CDCl₃, 500 MHz) δ 7.86 (s, 1H), 7.74-7.70 (m, 2H), 7.53 (s, 1H), 7.49-7.32 (m, 7H), 7.16 (d, 1H, J=8.5 Hz), 6.59 (s, 1H), 6.32 (s, 1H), 5.96 (s, 1H), 5.10 (s, 2H), 4.79 (s, 2H), 2.34 (s, 3H), 2.30 (s, 3H)

G4-12: ¹H NMR (CDCl₃, 500 MHz) δ 8.73 (s, 1H), 7.88 (s, 1H), 7.76-7.71 (m, 2H), 7.52 (s, 1H), 7.49-7.26 (m, 7H), 7.16 (d, 1H, J=8.0 Hz), 6.61 (s, 1H), 5.33 (s, 2H), 4.81 (s, 2H), 2.47 (s, 3H), 2.35 (s, 3H)

G4-13: ¹H NMR (CDCl₃, 500 MHz) δ 7.87 (s, 1H), 7.76-7.72 (m, 2H), 7.54 (s, 1H), 7.49-7.32 (m, 7H), 7.15 (d, 1H, J=8.0 Hz), 6.60 (s, 1H), 5.95 (s, 1H), 5.21 (s, 2H0, 4.87 (s, 2H), 2.41 (s, 3H), 2.35 (s, 3H)

Throughout this document, various references are mentioned. All such references are incorporated herein by reference, including the references set forth in the following list:

REFERENCES (1) Ciechanover, A. The ubiquitin-proteasome pathway: on protein death and cell life. *EMBO J.* 1998, 17, 7151-7160.

(2) Dick, T. P.; Nussbaum, A. K.; Deeg, M.; Heinemeyer, W.; Groll, M.; Schirle, M.; Keilholz, W.; Stevanovic, S.; Wolf, D. H.; Huber, R.; Rammensee, H. G.; Schild, H. Contribution of proteasomal beta-subunits to the cleavage of peptide substrates analyzed with yeast mutants. *J. Biol. Chem.* 1998, 273, 25637-25646.

(3) Angeles, A.; Fung, G.; Luo, H. Immune and non-immune functions of the immunoproteasome. *Front. Biosci.* 2012, 17, 1904-1916.

(4) Muchamuel, T.; Basler, M.; Aujay, M. A.; Suzuki, E.; Kalim, K. W.; Lauer, C.; Sylvain, C.; Ring, E. R.; Shields, J.; Jiang, J.; Shwonek, P.; Parlati, F.; Demo, S. D.; Bennett, M. K.; Kirk, C. J.; Groettrup, M. A selective inhibitor of the immunoproteasome subunit LMP7 blocks cytokine production and attenuates progression of experimental arthritis. *Nat. Med.* 2009, 15, 781-787.

(5) Kisselev, A. F.; Callard, A.; Goldberg, A. L. Importance of the different proteolytic sites of the proteasome and the efficacy of inhibitors varies with the protein substrate. *J. Biol. Chem.* 2006, 281, 8582-8590.

(6) Wehenkel, M.; Ban, J. O.; Ho, Y. K.; Carmony, K. C.; Hong, J. T.; Kim, K. B. A selective inhibitor of the immunoproteasome subunit LMP2 induces apoptosis in (7) Rock, K. L.; Goldberg, A. L. Degradation of cell proteins and the generation of MHC class I-presented peptides. *Annu. Rev. Immunol.* 1999, 17, 739-779.

(8) Parlati, F.; Lee, S. J.; Aujay, M.; Suzuki, E.; Levitsky, K.; Lorens, J. B.; Micklem, D. R.; Ruurs, P.; Sylvain, C.; Lu, Y.; Shenk, K. D.; Bennett, M. K. Carfilzomib can induce tumor cell death through selective inhibition of the chymotrypsin-like activity of the proteasome. *Blood* 2009, 114, 3439-3447.

(9) Adams, J. The development of proteasome inhibitors as anticancer drugs. *Cancer Cell* 2004, 5, 417-421.

(10) Kim, K. B.; Crews, C. M. From epoxomicin to carfilzomib: chemistry, biology, and medical outcomes. *Nat. Prod. Rep.* 2013, 30, 600-604.

(11) Vij, R.; Wang, M.; Kaufman, J. L.; Lonial, S.; Jakubowiak, A. J.; Stewart, A. K.; Kukreti, V.; Jagannath, S.; McDonagh, K. T.; Alsina, M.; Bahlis, N. J.; Reu, F. J.; Gabrail, N. Y.; Belch, A.; Matous, J. V.; Lee, P.; Rosen, P.; Sebag, M.; Vesole, D. H.; Kunkel, L. A.; Wear, S. M.; Wong, A. F.; Orlowski, R. Z.; Siegel, D. S. An open-label, single-arm, phase 2 (PX-171-004) study of single-agent carfilzomib in bortezomib-naive patients with relapsed and/or refractory multiple myeloma. *Blood* 2012, 119, 5661-5670.

(12) Herndon, T. M.; Deisseroth, A.; Kaminskas, E.; Kane, R. C.; Koti, K. M.; Rothmann, M. D.; Habtemariam, B.; Bullock, J.; Bray, J. D.; Hawes, J.; Palmby, T. R.; Jee, J.; Adams, W.; Mahayni, H.; Brown, J.; Dorantes, A.; Sridhara, R.; Farrell, A. T.; Pazdur, R. U.S. Food and Drug Administration approval: carfilzomib for the treatment of multiple myeloma. *Clin. Cancer Res.* 2013, 19, 4559-4563.

(13) McBride, A.; Ryan, P. Y. Proteasome inhibitors in the treatment of multiple myeloma. *Expert Rev. Anticancer Ther.* 2013, 13, 339-358.

(14) Cvek, B. Proteasome inhibitors. *Prog. Mol. Biol. Transl. Sci.* 2012, 109, 161-226.

(15) Chen, D.; Frezza, M.; Schmitt, S.; Kanwar, J.; Dou, Q. P. Bortezomib as the first proteasome inhibitor anticancer drug: current status and future perspectives. *Curr. Cancer Drug Targets* 2011, 11, 239-253.

(16) Richardson, P. G.; Barlogie, B.; Berenson, J.; Singhal, S.; Jagannath, S.; Irwin, D.; Rajkumar, S. V.; Srkalovic, G.; Alsina, M.; Alexanian, R.; Siegel, D.; Orlowski, R. Z.; Kuter, D.; Limentani, S. A.; Lee, S.; Hideshima, T.; Esseltine, D. L.; Kauffman, M.; Adams, J.; Schenkein, D. P.; Anderson, K. C. A phase 2 study of bortezomib in relapsed, refractory myeloma. *N. Engl. J. Med.* 2003, 348, 2609-2617.

(17) Siegel, D. S.; Martin, T.; Wang, M.; Vij, R.; Jakubowiak, A. J.; Lonial, S.; Trudel, S.; Kukreti, V.; Bahlis, N.; Alsina, M.; Chanan-Khan, A.; Buadi, F.; Reu, F. J.; Somlo, G.; Zonder, J.; Song, K.; Stewart, A. K.; Stadtmauer, E.; Kunkel, L.; Wear, S.; Wong, A. F.; Orlowski, R. Z.; Jagannath, S. A phase 2 study of single-agent carfilzomib (PX-171-003-A1) in patients with relapsed and refractory multiple myeloma. *Blood* 2012, 120, 2817-2825.

(18) Yang, J.; Wang, Z.; Fang, Y.; Jiang, J.; Zhao, F.; Wong, H.; Bennett, M. K.; Molineaux, C. J.; Kirk, C. J. Pharmacokinetics, pharmacodynamics, metabolism, distribution, and excretion of carfilzomib in rats. *Drug Metab. Dispos.* 2011, 39, 1873-1882.

(19) Papadopoulos, K. P.; Burris, H. A., 3rd; Gordon, M.; Lee, P.; Sausville, E. A.; Rosen, P. J.; Patnaik, A.; Cutler, R. E., Jr.; Wang, Z.; Lee, S.; Jones, S. F.; Infante, J. R. A phase I/II study of carfilzomib 2-10-min infusion in patients with advanced solid tumors. *Cancer Chemother. Pharmacol.* 2013, 72, 861-868.

(20) Wang, Z.; Yang, J.; Kirk, C.; Fang, Y.; Alsina, M.; Badros, A.; Papadopoulos, K.; Wong, A.; Woo, T.; Bomba, D.; Li, J.; Infante, J. R. Clinical pharmacokinetics, metabolism, and drug-drug interaction of carfilzomib. *Drug Metab. Dispos.* 2013, 41, 230-237.

(21) Uttamsingh, V.; Lu, C.; Miwa, G.; Gan, L. S. Relative contributions of the five major human cytochromes P450, 1A2, 2C9, 2C19, 2D6, and 3A4, to the hepatic metabolism of the proteasome inhibitor bortezomib. *Drug Metab. Dispos.* 2005, 33, 1723-1728.

(22) Hemeryck, A.; Geerts, R.; Monbaliu, J.; Hassler, S.; Verhaeghe, T.; Diels, L.; Verluyten, W.; van Beijsterveldt, L.; Mamidi, R. N.; Janssen, C.; De Coster, R. Tissue distribution and depletion kinetics of bortezomib and bortezomib-related radioactivity in male rats after single and repeated intravenous injection of 14 C-bortezomib. *Cancer Chemother. Pharmacol.* 2007, 60, 777-787.

(23) Kasam, V.; Lee, N. R.; Kim, K. B.; Zhan, C. G. Selective immunoproteasome inhibitors with non-peptide scaffolds identified from structure-based virtual screening. *Bioorg. Med. Chem. Lett.* 2014, 24, 3614-3617.

(24) Lei, B.; Abdul Hameed, M. D.; Hamza, A.; Wehenkel, M.; Muzyka, J. L.; Yao, X. J.; Kim, K. B.; Zhan, C. G. Molecular basis of the selectivity of the immunoproteasome catalytic subunit LMP2-specific inhibitor revealed by molecular modeling and dynamics simulations. *J. Phys. Chem. B* 2010, 114, 12333-12339.

(25) Kisselev, A. F.; Goldberg, A. L. Monitoring activity and inhibition of 26S proteasomes with fluorogenic peptide substrates. *Methods Enzymol.* 2005, 398, 364-378.

(26) Shah, P. P.; Myers, M. C.; Beavers, M. P.; Purvis, J. E.; Jing, H.; Grieser, H. J.; Sharlow, E. R.; Napper, A. D.; Huryn, D. M.; Cooperman, B. S.; Smith, A. B., 3rd; Diamond, S. L. Kinetic characterization and molecular docking of a novel, potent, and selective slow-binding inhibitor of human cathepsin L. *Mol. Pharmacol.* 2008, 74, 34-41.

(27) Huber, E. M.; Groll, M Inhibitors for the immuno- and constitutive proteasome: current and future trends in drug development. *Angew. Chem., Int. Ed.* 2012, 51, 8708-8720.

(28) Beck, P.; Dubiella, C.; Groll, M. Covalent and non-covalent reversible proteasome inhibition. *Biol. Chem.* 2012, 393, 1101-1120.

(29) Arastu-Kapur, S.; Anderl, J. L.; Kraus, M.; Parlati, F.; Shenk, K. D.; Lee, S. J.; Muchamuel, T.; Bennett, M. K.; Driessen, C.; Ball, A. J.; Kirk, C. J. Nonproteasomal targets of the proteasome inhibitors bortezomib and carfilzomib: a link to clinical adverse events. *Clin. Cancer Res.* 2011, 17, 2734-2743.

(30) Reece, D. E.; Sullivan, D.; Lonial, S.; Mohrbacher, A. F.; Chatta, G.; Shustik, C.; Burris, H., 3rd; Venkatakrishnan, K.; Neuwirth, R.; Riordan, W. J.; Karol, M.; von Moltke, L. L.; Acharya, M.; Zannikos, P.; Keith Stewart, A. Pharmacokinetic and pharmacodynamic study of two doses of bortezomib in patients with relapsed multiple myeloma. *Cancer Chemother. Pharmacol.* 2011, 67, 57-67.

(31) Lansdell, T. A.; Hurchla, M. A.; Xiang, J.; Hovde, S.; Weilbaecher, K. N.; Henry, R. W.; Tepe, J. J. Noncompetitive modulation of the proteasome by imidazoline

(32) Gallastegui, N.; Beck, P.; Arciniega, M.; Huber, R.; Hillebrand, S.; Groll, M. Hydroxyureas as noncovalent proteasome inhibitors. *Angew. Chem., Int. Ed.* 2012, 51, 247-249.

(33) Azevedo, L. M.; Lansdell, T. A.; Ludwig, J. R.; Mosey, R. A.; Woloch, D. K.; Cogan, D. P.; Patten, G. P.; Kuszpit, M. R.; Fisk, J. S.; Tepe, J J Inhibition of the human proteasome by imidazoline scaffolds. *J. Med. Chem.* 2013, 56, 5974-5978.

(34) Basse, N.; Montes, M.; Marechal, X.; Qin, L.; Bouvier-Durand, M.; Genin, E.; Vidal, J.; Villoutreix, B. O.; Reboud-Ravaux, M. Novel organic proteasome inhibitors identified by virtual and in vitro screening. *J. Med. Chem.* 2010, 53, 509-513.

(35) Kikuchi, J.; Shibayama, N.; Yamada, S.; Wada, T.; Nobuyoshi, M.; Izumi, T.; Akutsu, M.; Kano, Y.; Sugiyama, K.; Ohki, M.; Park, S. Y.; Furukawa, Y. Homopiperazine derivatives as a novel class of proteasome inhibitors with a unique mode of proteasome binding. *PLoS One* 2013, 8, e60649.

(36) Kawamura, S.; Unno, Y.; List, A.; Mizuno, A.; Tanaka, M.; Sasaki, T.; Arisawa, M.; Asai, A.; Groll, M.; Shuto, S. Potent proteasome inhibitors derived from the unnatural cis-cyclopropane isomer of belactosin A: synthesis, biological activity, and mode of action. *J. Med. Chem.* 2013, 56, 3689-3700.

(37) Mroczkiewicz, M.; Winkler, K.; Nowis, D.; Placha, G.; Golab, J.; Ostaszewski, R. Studies of the synthesis of all stereoisomers of MG-132 proteasome inhibitors in the tumor targeting approach. *J. Med. Chem.* 2010, 53, 1509-1518.

(38) Huber, E. M.; Basler, M.; Schwab, R.; Heinemeyer, W.; Kirk, C. J.; Groettrup, M.; Groll, M. Immuno- and constitutive proteasome crystal structures reveal differences in substrate and inhibitor specificity. *Cell* 2012, 148, 727-738.

(39) Trott, O.; Olson, A. J. AutoDock Vina: improving the speed and accuracy of docking with a new scoring function, efficient optimization, and multithreading. *J. Comput. Chem.* 2010, 31, 455-461.

(40) Zhou, H. J.; Aujay, M. A.; Bennett, M. K.; Dajee, M.; Demo, S. D.; Fang, Y.; Ho, M. N.; Jiang, J.; Kirk, C. J.; Laidig, G. J.; Lewis, E. R.; Lu, Y.; Muchamuel, T.; Parlati, F.; Ring, E.; Shenk, K. D.; Shields, J.; Shwonek, P. J.; Stanton, T.; Sun, C. M.; Sylvain, C.; Woo, T. M.; Yang, J. Design and synthesis of an orally bioavailable and selective peptide epoxyketone proteasome inhibitor (PR-047). *J. Med. Chem.* 2009, 52, 3028-3038.

(41) Williamson, M. J.; Silva, M. D.; Terkelsen, J.; Robertson, R.; Yu, L.; Xia, C.; Hatsis, P.; Bannerman, B.; Babcock, T.; Cao, Y.; Kupperman, E. The relationship among tumor architecture, pharmacokinetics, pharmacodynamics, and efficacy of bortezomib in mouse xenograft models. *Mol. Cancer Ther* 2009, 8, 3234-3243.

(42) Papandreou, C. N.; Daliani, D. D.; Nix, D.; Yang, H.; Madden, T.; Wang, X.; Pien, C. S.; Millikan, R. E.; Tu, S. M.; Pagliaro, L.; Kim, J.; Adams, J.; Elliott, P.; Esseltine, D.; Petrusich, A.; Dieringer, P.; Perez, C.; Logothetis, C. J. Phase I trial of the proteasome inhibitor bortezomib in patients with advanced solid tumors with observations in androgen-independent prostate cancer. *J. Clin. Oncol.* 2004, 22, 2108-2121.

(43) 1. Kim, K. B.; Fonseca, F. N.; Crews, C. M. Development and characterization of proteasome inhibitors. Methods Enzymol 2005, 399, 585-609.

(44) Myung, J.; Kim, K. B.; Lindsten, K.; Dantuma, N. P.; Crews, C. M. Lack of proteasome active site allostery as revealed by subunit-specific inhibitors. Mol Cell 2001, 7, 411-420.

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:
1. A compound of the formula:

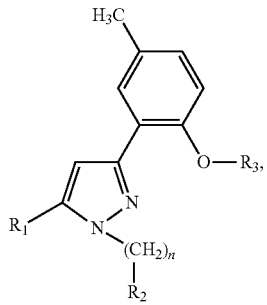

or a pharmaceutically-acceptable salt thereof, wherein $R_1$ is selected from

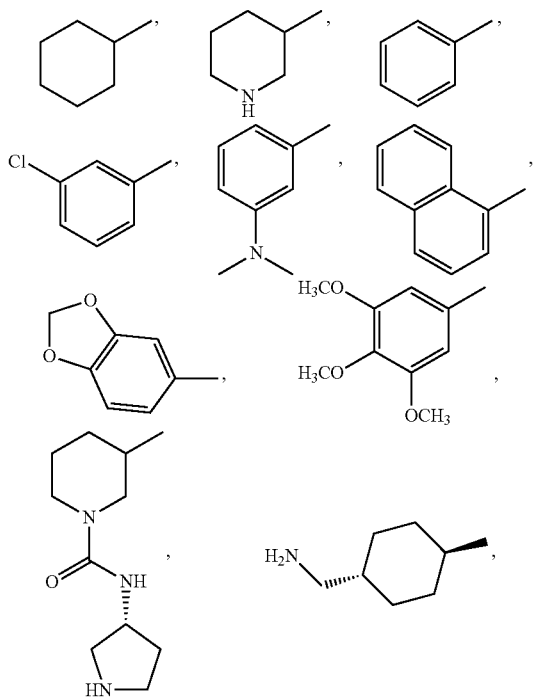

-continued
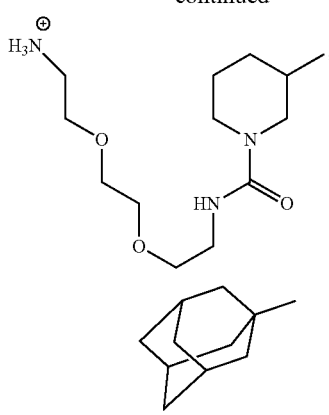
R₂ is selected from
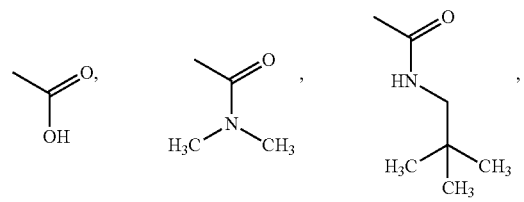
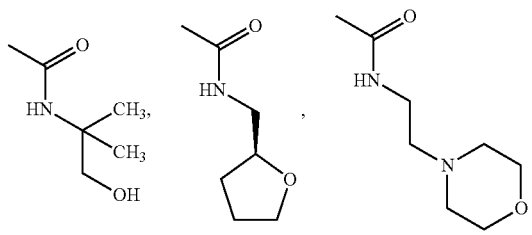
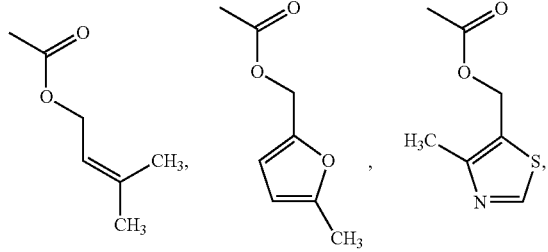
-continued
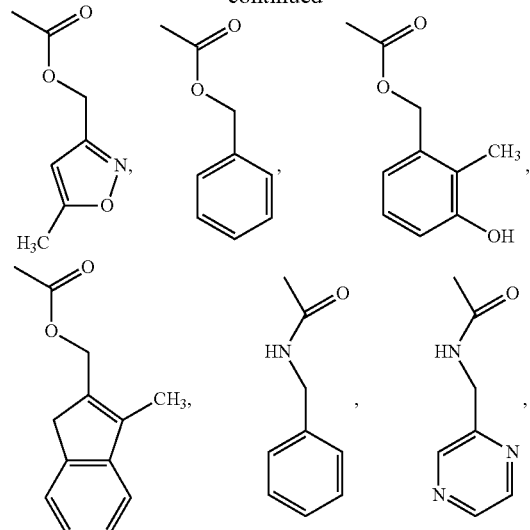
R₃ is selected from
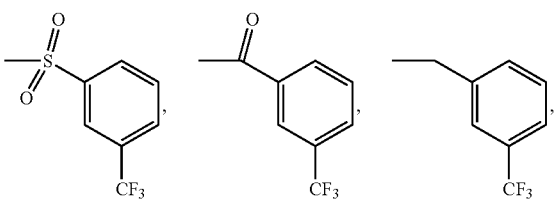

and
n is 0, 1, or 2.

2. The compound of claim 1, wherein $R_1$ is selected from [structures shown] and

3. The compound of claim 2, wherein $R_2$ is selected from [structures shown]

and n is 0 or 1.

4. The compound of claim 3, wherein $R_3$ is selected from [structures shown]

and

5. The compound of claim 2, wherein $R_3$ is selected from [structure shown]

and
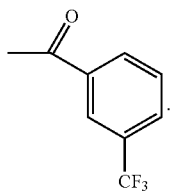
6. The compound of claim 2, wherein $R_2$ is
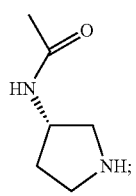
and n is 0 or 1.
7. The compound of claim 6, wherein $R_3$ is
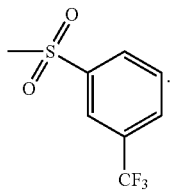
8. The compound of claim 2, wherein $R_3$ is
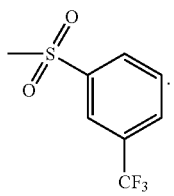
9. The compound of claim 1, according to a formula selected from the group consisting of:
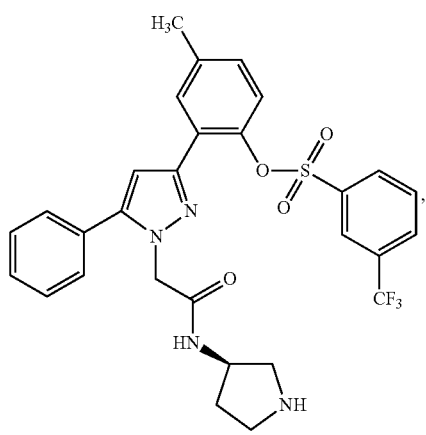
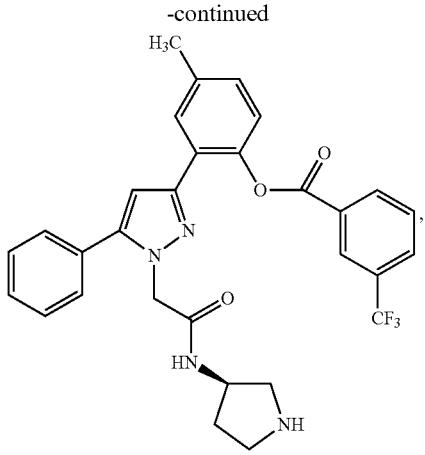
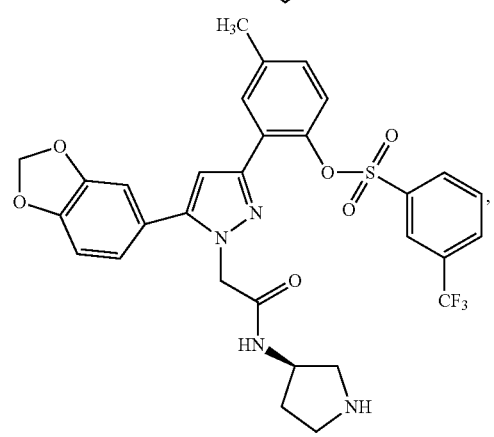
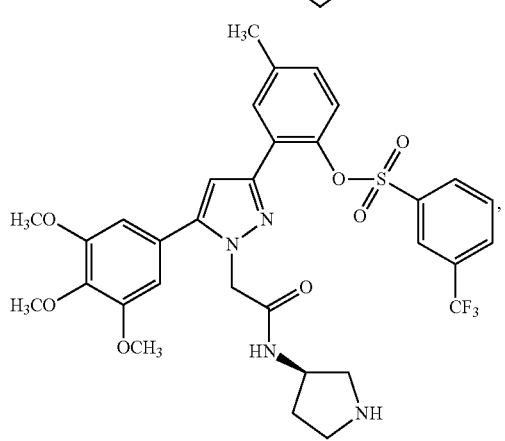
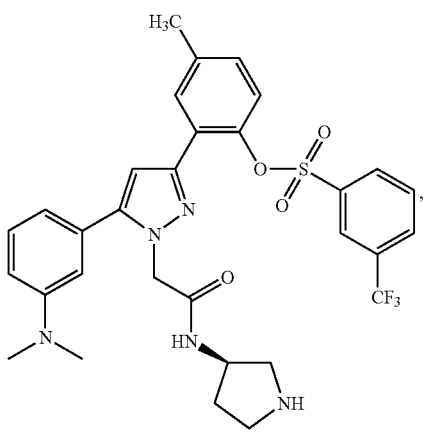

-continued
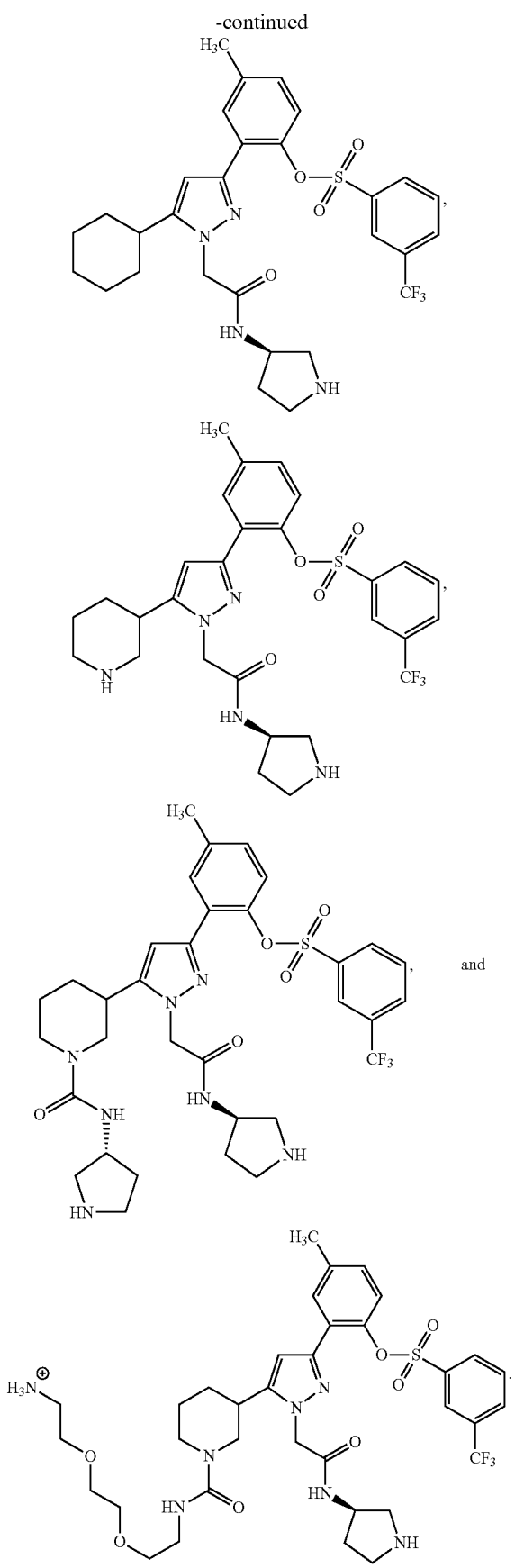
and
10. The compound of claim 1, according to the formula
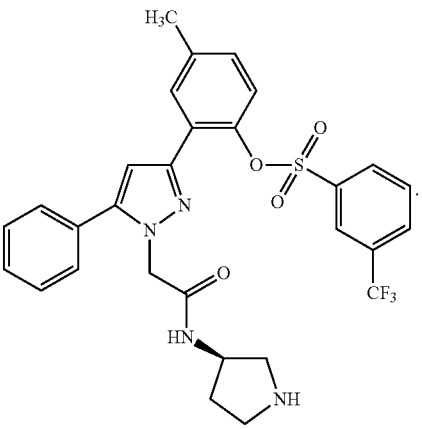 [SMILES: Cc1ccc(OS(=O)(=O)c2cccc(C(F)(F)F)c2)c(-c2cc(-c3ccccc3)n(CC(=O)N[C@@H]3CCNC3)n2)c1]
11. The compound of claim 1, according to the formula
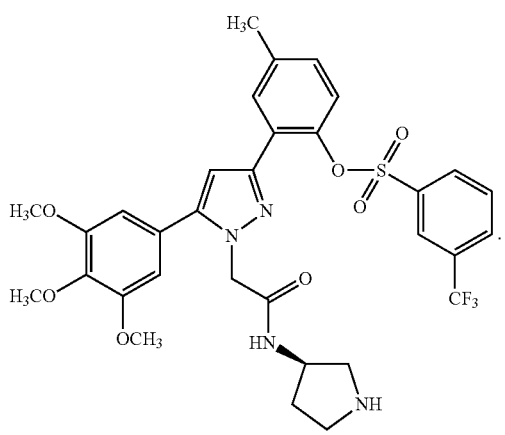 [SMILES: COc1cc(-c2cc(-c3cc(C)ccc3OS(=O)(=O)c3cccc(C(F)(F)F)c3)nn2CC(=O)N[C@@H]2CCNC2)cc(OC)c1OC]
12. The compound of claim 1, according to the formula
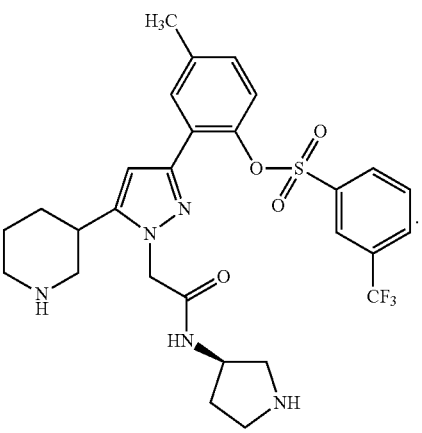 [SMILES: Cc1ccc(OS(=O)(=O)c2cccc(C(F)(F)F)c2)c(-c2cc(C3CCCNC3)n(CC(=O)N[C@@H]3CCNC3)n2)c1]

13. The compound of claim 1, according to the formula

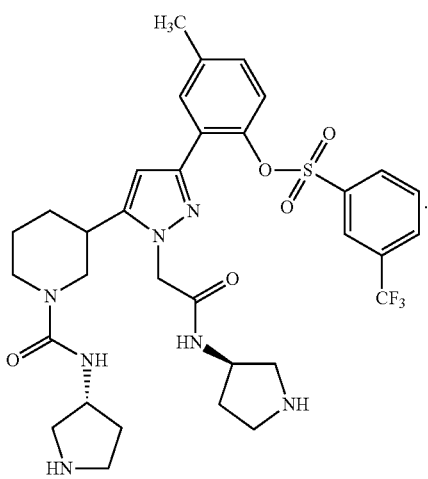 [SMILES: Cc1ccc(OS(=O)(=O)c2cccc(C(F)(F)F)c2)c(-c2cc(C3CCCN(C(=O)N[C@@H]4CCNC4)C3)n(CC(=O)N[C@@H]3CCNC3)n2)c1]

14. The compound of claim 1, according to the formula

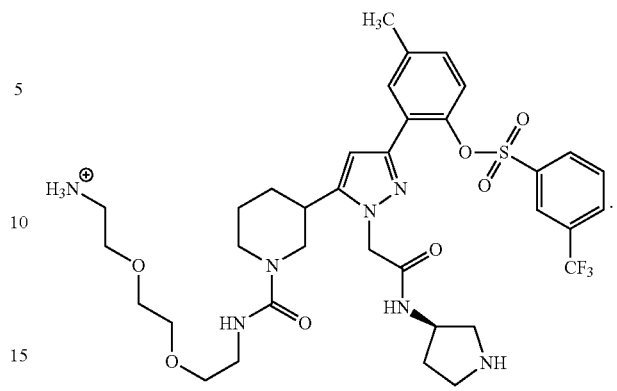

15. A pharmaceutical composition, comprising: the compound of claim 1, and a pharmaceutically-acceptable carrier.

16. A method of inhibiting a 26S proteasome in a cell, comprising administering an effective amount of the compound of claim 1 to the cell.

17. The method of claim 16, wherein the administering the compound to the cell leads to apoptosis of the cell.

18. The method of claim 16, wherein the cell is a cancer cell.

19. A method of treating a 26S proteasome-mediated disease in a subject comprising administering an effective amount of a pharmaceutical composition containing the compound of claim 1 to the subject.

20. The method of claim 19, wherein the subject is in need of treatment for cancer.

\* \* \* \* \*